United States Patent [19]

Gupta et al.

[11] Patent Number: 4,990,499
[45] Date of Patent: Feb. 5, 1991

[54] ANTI-HERPES SIMPLEX VIRUS ACTIVITY OF 5-ALKOXYMETHYL-2'-DEOXYCYTIDIMES AND THEIR 5-MONOPHOSPHATES

[75] Inventors: Vidya S. Gupta; Guy Tourigny; Philip J. Aduma; Allan L. Stuart, all of Saskatoon, Canada

[73] Assignee: University of Saskatchewan, Saskatchewan, Canada

[21] Appl. No.: 448,944

[22] Filed: Dec. 12, 1989

[30] Foreign Application Priority Data

Sep. 29, 1989 [CA] Canada ................................. 615352

[51] Int. Cl.$^5$ .................... A61K 31/70; C07H 19/067; C07H 19/073; C07H 19/173
[52] U.S. Cl. ........................................ 514/49; 514/51; 536/23; 536/24; 536/29
[58] Field of Search ..................... 514/49, 51; 536/23, 536/29

[56] References Cited

PUBLICATIONS

Goodman, L., "Chemical Syntheses and Transformations of Nucleosides" in Basic Principles in Nucleic Acid Chemistry, P.O.P.Ts'O ed., Academic Press., New York., 1974, vol. 1, See pp. 151–152.

Mehta et al., Ann. N. Y. Acad. Sci., 255, 559–563 (1975).

Leung et al., Biochem. Medicine, 9(3), 237–43 (1974).

Primary Examiner—Johnnie R. Brown
Assistant Examiner—L. Eric Crane
Attorney, Agent, or Firm—Nixon & Vanderhye

[57] ABSTRACT 5-alkoxymethyl-2'-deoxycytidines, particularly 5-methoxymethyl-2'-deoxycytidine, are useful in the treatment of infections caused by Herpes simplex virus and the treatment of neoplasms in which Herpes simplex virus is implicated.

22 Claims, 9 Drawing Sheets

EFFECT OF A-105(MMdCyd) AND A-105+H$_4$dUrd on PRODUCTION OF INFECTIOUS VIRUS PARTICLES (VIRUS RELEASE) VIRUS INPUT 20 PFU.

REVERSAL OF THE ANTIVIRAL POTENCY OF MMdCyd BY NATURAL PYRIMIDINE DEOXYNUCLEOSIDES.

REVERSAL OF THE ANTIVIRAL POTENCY OF MMdCyd BY EQUIMOLAR CONCENTRATIONS OF 2'-DEOXYCYTIDINE.(dCyd)

REVERSAL OF THE ANTIVIRAL ACTIVITY OF MMdCyd BY 2'-DEOXYURIDINE (dUrd).

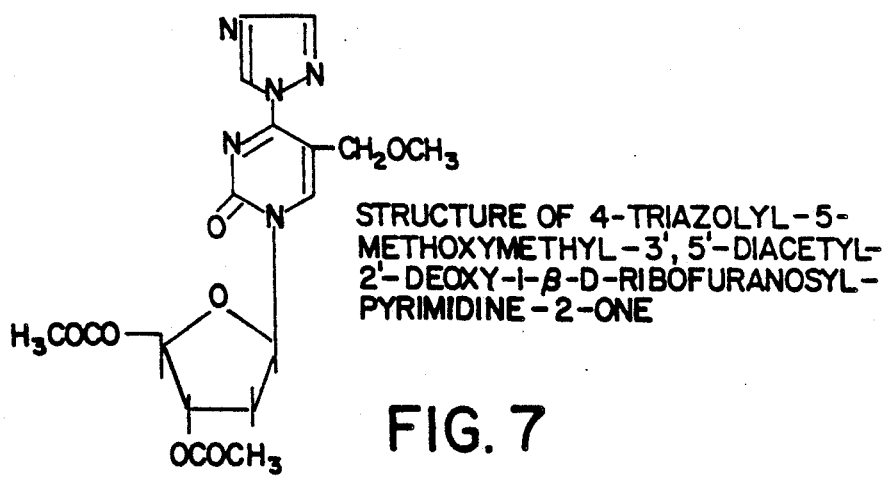
FIG. 7 STRUCTURE OF 4-TRIAZOLYL-5-METHOXYMETHYL-3',5'-DIACETYL-2'-DEOXY-1-β-D-RIBOFURANOSYL-PYRIMIDINE-2-ONE
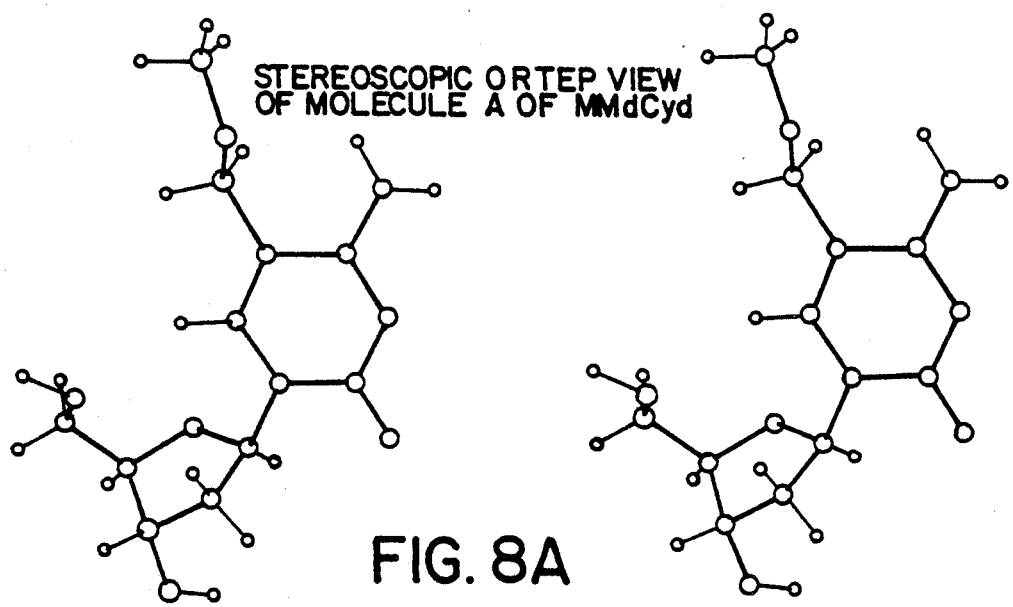
FIG. 8A STEREOSCOPIC ORTEP VIEW OF MOLECULE A OF MMdCyd
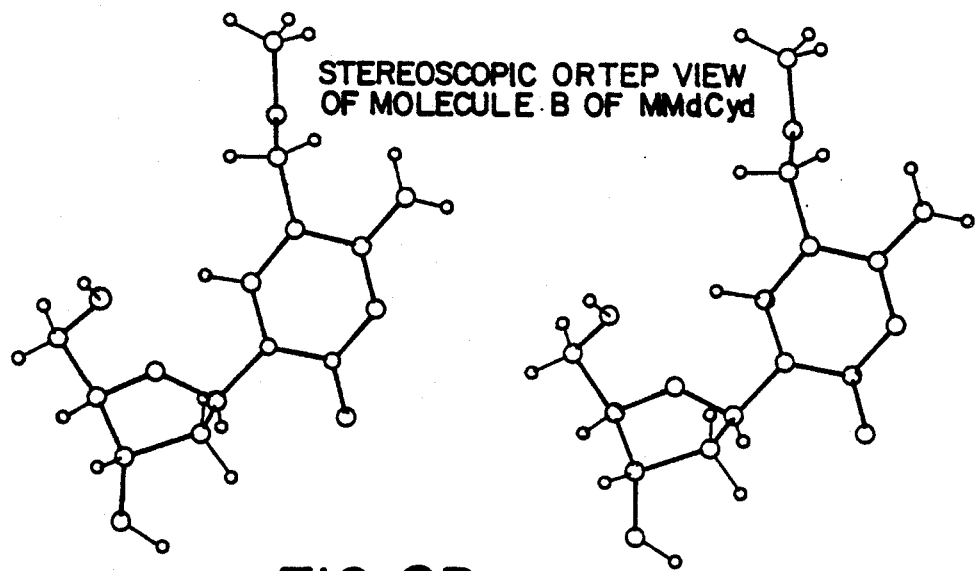
FIG. 8B STEREOSCOPIC ORTEP VIEW OF MOLECULE B OF MMdCyd POTENTIATION OF THE ANTIVIRAL ACTIVITY OF MMdCyd BY 2'-DEOXYGUANOSINE (dGuo) AND TETRAHYDRODROXYURIDINE ($H_4$dUrd)

EFFECT ON PRODUCTION OF INFECTIOUS VIRUS PARTICLES AT DIFFERENT TIMES OF THE INFECTIOUS PROCESS BY VARIOUS TREATMENTS.

HSV-1, DNA POLYMERASE CATALYZED INCOROPORATION OF [$^{-3}$H] dAMP INTO CALFTHYMUS DNA TEMPLATE-PRIMER WITH dCPT OR MMdCTP AS THE RATE LIMITING SUBSTRATE

EFFECTS OF PURINE DEOXYNUCLEOSIDES ON HSV-1 PLAQUE REDUCTION

ANTI-HERPES SIMPLEX VIRUS ACTIVITY OF 5-ALKOXGMETHYL-2'-DEOXYCYTIDIMES AND THEIR 5-MONOPHOSPHATES

The present invention is concerned with treatment of infections caused by the Herpes simplex virus and also the treatment of neoplasms in which Herpes simplex virus is implicated.

BACKGROUND OF THE INVENTION

Herpes simplex type 1 (HSV-1) is a source of frequent infection in humans with varying degree of severity from mild discomfort (recurrent HSV labialis) to serious ocular infection including impairment of vision (Herpes keratitis) and life-threatening disease (Herpes encephalitis). Ten to fifteen percent of the population on the North American continent over the age of 18 years have recurrent Herpes infections three or more times every year (Maugh, 1976). (References appear at the end of the disclosure)

A wide variety of drugs has been tested for antiviral activity against Herpes viruses and few have been licensed for use in humans (for reviews see Corey et al., 1983; Corey and Spears, 1986; DeClercq, 1982; Hirsch and Schooley, 1983; Whitley et al., 1986). The most significant developments in the last ten years have been the discovery of drugs which elicit antiviral activity by selectively utilizing or inhibiting virus specified functions to a greater degree than host cells (Babiuk et al., 1975; DeClercq et al., 1979; Elion et al., 1977; Gupta, 1979, 1981; Helgstrand et al., 1978; and Lopez et al., 1980). This new generation of antiviral drugs includes compounds such as acyclovir, 5-bromovinyl-2'-deoxyuridine (BVdUrd), 5-ethyl-2'-deoxyuridine (EtdUrd), 5-methoxymethyl-2'-deoxyuridine and 5-iodo-2-fluoroaracytosine. The selectivity of these compounds is primarily due to specific interaction with two virus-induced enzymes, deoxythymidine-deoxycytidine (dThd/dCyd) kinase and DNA polymerase.

There are many patents and published patent applications relating to antiviral nucleosides. For instance, U.S. Pat. Nos. 4,808,614 and 4,692,434 (Hertel) relate to various 2'-deoxy-2',2'-difluoro nucleosides and their use as antiviral agents, particularly their use against Herpes simplex virus, type I.

U.S. Pat. No. 4,788,181 (Driscoll et al) relates to 2',3'-dideoxy-5-azcytidine and 5-methyl-, 5-bromo- and 5-fluoro-2',3'-dideoxycytidine and their phosphorylated derivatives for use against RNA viruses and DNA viruses, particularly Human Immunodeficiency Virus.

U.S. Pat. No. 4,382,925 (DeClercq et al) relates to the compounds E-5-(2-bromovinyl)-2'-deoxycytidine and E-5-(2-iodovinyl)-2'-deoxycytidine and their antiviral activity which is said to be very specific towards Herpes simplex virus.

PCT Application No. W087/04929 (Greer et al) is directed to the use of 5-substituted-2'-deoxycytidine in the treatment or prevention of retroviral diseases, particularly AIDS. The substituent at the 5-position is fluorine or chlorine or a methyl or trifluoromethyl group.

U.S. Pat. No. 4,210,638 (Greer) discloses pharmaceutical compositions containing 5-trifluoromethyl-2'-deoxycytidine and a cytidine deaminase inhibitor, for treating diseases caused by Herpes or Herpes-like viruses.

U.S. Pat. No. 4,230,698 (Bobek et al) is concerned with 2-substituted arabinofuranosyl nucleosides and nucleotides which are said to have useful antitumour, antiviral and antimicrobial activities. The 2-substituted arabinofuranosyl nucleosides and nucleotides are said to have been developed when searching for deaminase resistant antitumour agents.

DE No. 3002197 (Gauri) discloses 5-alkyl and 5-alkenyl substituted pyrimidine nucleosides, which can be substituted by halogen in the 5-alkyl or 5-alkenyl substituent, as virostatic and cytostatic agents.

EP No. 0216511 (Mitsuya et al) relates to the inhibition of in vitro infectivity and the cytopathic effect of HTLV-111/LAV by 2',3'-dideoxynucleosides, particularly 2',3'-dideoxycytidine and the related mono- and tri-phosphates.

PCT Application No. WO 88/09796 (Webb) is concerned with epoxide, episulphide and aziridine derivatives of nucleoside analogues and their use for the treatment or prophylaxis of retroviral infections, including AIDS.

PCT Application WO 88/00050 (Eriksson et al) discloses the use of 2',3'-dideoxy-3'-fluoro nucleosides for the control or treatment of retrovirus and hepatitis B infections.

EP 0217580 (Rideout et al) is concerned with certain novel 3'-azidonucleosides and their use in therapy, particularly the treatment and prophylaxis of gram negative bacterial infections and retroviral infections such as AIDS.

EP No. 0206497 (Koszalka et al) discloses certain 2',3'-dideoxynucleosides and their use in treatment and prophylaxis of viral, especially retroviral infections.

EP No. 0294113 (Kremitsky et al) discloses derivatives of 2',3'-dideoxycytidine in which the N4-position of the dideoxycytidine is substituted by an acyl group and/or the 5'-O-position is substituted by a $C_{3-5}$ alkanoyl group. These compounds are said to be useful for the treatment or prophylaxis of viral infections, particularly retroviral infections and especially AIDS, and to show improved bioavailability over 2',3'-didoexycytidine.

EP No. 0311100 (Partridge et al) is concerned with derivatives of 2',3'-dideoxycytidine and 2'3'-didehydro-2',3'-dideoxycytidine and their use against retroviral infections, especially AIDS.

EP No. 0307914 (Soo) is concerned with 2',3'-dideoxy analogues of adenosine, thymidine, cytidine, guanosine, uridine or inosine which are said to be effective in preventing AIDS in extremely low dosages at which they exhibit no neuropathic effects.

EP No. 0254268 (Matthes et al) discloses certain 3'-deoxy-3'-fluoro nucleosides, including some which are substituted at the 5-position of the cytidine moiety, and their use to combat AIDS.

EP No. 0284405 (Frost) discloses phosphate bridged dimers of nucleoside derivatives for use as antiviral agents.

EP No. 0286413 (Weinstein) discloses the administration of phosphorylated nucleosides encapsulated in liposomes in the prevention or treatment of diseases caused by retroviruses, particularly AIDS.

EP No. 0310673 (Ueda et al) discloses novel 2'-alkylidenepyrimidine nucleoside derivatives and their use as antiviral agents.

In spite of the recent advances there is a definite need of new drugs to treat HSV-associated diseases for the following reasons:

(i) there is no drug approved for the treatment of Herpes labialis;

(ii) there is a definite need of better drugs for the treatment of Herpes encephalitis;

(iii) deoxyuridine analogues (BVdUrd and EtdUrd) are metabolically unstable, and poorly cross the blood brain barrier. Thus, these compounds are of limited usefulness in the treatment of systemic Herpes simplex infections;

(iv) currently approved antiherpes drugs, such as acyclovir, arabinosyl adenine, trifluorothymidine, are not useful for the treatment of recurrent HSV infections in patients.

SUMMARY OF THE INVENTION

The present invention relates to a class of novel compounds that are 5-alkoxymethyl-2'-deoxycytidines, their pharmaceutically acceptable salts, the phosphate derivatives thereof and their use in the treatment of infections caused by Herpes simplex virus and neoplasm in patients in which Herpes simplex virus is implicated. The invention also extends to prodrugs of the active nucleoside that release the active nucleoside in vivo and thus prolong its sojourn in the body. Mention is made of N4-acylated compounds, particularly compounds in which the acyl group is derived from an alkanoic acid having from 3 to 7 carbon atoms. Examples of such compounds include the N4-propanoyl and the N4-pivaloyl compounds.

The compounds can be used in the form of their salts with any suitable acid. Suitable acids will be known to those skilled in the art and include, for example inorganic acids such as hydrochloric acid, sulfuric acid, phosphoric acid, and organic acids such as lactic acid, citric acid, gluconic acid, succinc acid and lactobromic acid.

The alkoxy group that is present as part of the 5-alkoxymethyl group preferably contains up to 4 carbon atoms, although most preferably it has only one carbon atom. The preferred compound of the invention, 5-methoxymethyl-2'-deoxycytidine, (MMdCyd), is the compound of formula

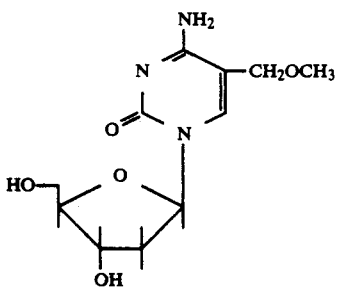

DESCRIPTION OF THE PREFERRED EMBODIMENTS

MMdCyd can be obtained from 5-methoxymethyl-2'-deoxyuridine by replacing the oxo group at the 4-position of the uridine moiety with a good leaving group and then replacing the leaving group with an amino group. Suitable leaving groups include triazolyl, sulfonates such as mesylate and tosylate, and halides. The hydroxy groups present in the 3'- and 5'-positions of the uridine are suitably protected during the reactions, for example by acetylation, followed by deacetylation with methanolic ammonia. Other 5-alkoxymethyl-2'-deoxycytidines can be obtained in similar manner from the corresponding 5-alkoxymethyl-2'-deoxyuridines.

The process for obtaining the compounds of the invention can be expressed in general form as a reaction between a compound of formula Y

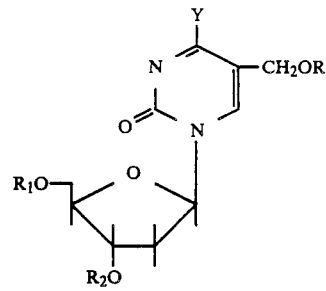

wherein R is an alkyl group having 1 to 4 carbon atoms, Y is a leaving group and $R_1$ and $R_2$ are both protecting groups, with an aminating agent to replace the leaving group by an amino group, followed by removal of the protecting groups. A suitable aminating agent is ammonia, in a solvent such as methanol or dioxane. The compound can be converted into a pharmaceutically acceptable salt.

Abbreviations used in this specification include the following:

| | |
|---|---|
| AI | antiviral indices |
| CMP | cytidine monophosphate |
| cpm | counts per minute |
| Cyd | cytidine |
| dGuo | 2'-deoxyguanosine |
| DiAcMMdCyd | 5-methoxymethyl-3',5'-diacetyl-2'-deoxycytidine |
| DiAcMMdUrd | 5-methoxymethyl-3',5'-diacetyl-2'-deoxyuridine |
| dATP | 2'-deoxyadenosine triphosphate |
| dCDP | 2'-deoxycytidine diphosphate |
| dCMP | 2'-deoxycytidine monophosphate |
| dCTP | 2'-deoxycytidine triphosphate |
| dCyd | 2'-deoxycytidine |
| dNTP | 2'-deoxyribonucleoside triphosphate |
| dUMP | 2'-deoxyuridine monophosphate |
| dTDP | 2'-deoxythymidine diphosphate |
| dThd | 2'-deoxyribosylthymidine (thymidine) |
| dTTP | 2'-deoxythymidine triphosphate |
| HSV | Herpes simplex virus |
| [$^3$H]dAMP | tritium labelled 2'-deoxyadenosine monophosphate |
| $H_4$dUMP | tetrahydro-2'-deoxyuridine monophosphate |
| $H_4$dUrd | tetrahydro-2'-deoxyuridine |
| $H_4$Urd | tetrahydrouridine |
| $K_i$ | Inhibitor constant |
| $K_m$ | Michaelis Menten constant |
| MTC | minimum toxic concentration |
| MEM | minimal essential medium |
| MMdCMP | 5-methoxymethyl-2'-deoxycytidine monophosphate |
| MMdCDP | 5-methoxymethyl-2'-deoxycytidine diphosphate |
| MMdCTP | 5-methoxymethyl-2'-deoxycytidine triphosphate |
| MMdCyd | 5-methoxymethyl-2'-deoxycytidine |
| MMdUMP | 5-methoxymethyl-2'-deoxyuridine monophosphate |
| MMdUrd | 5-methoxymethyl-2'-deoxyuridine |
| N-Me-MMdCyd | 5-methoxymethyl-N4-methyl-2'-deoxycytidine |
| N-Me-MMdCMP | 5-methoxymethyl-N4-methyl-2'deoxycytidine-5'-monophosphate |
| MedCyd | 5-methyl-2'-deoxycytidine |
| PFU | plaque forming units |
| Ura | uracil |

Depending upon the condition to be treated, the MMdCyd may be used with a deaminase inhibitor. Suitable deaminase inhibitors include, for instance, H$_4$Urd, H$_4$dUrd, ribofuranosyl-2H-1,3-diazepin-2-one derivatives (Marquez et al, 1980; Tiu et al, 1981) and ribofuranosyl-2(1H)-pyrimidinone derivatives (Kim et al 1986), of which H$_4$Urd and H$_4$dUrd are preferred. The MMdCyd, either with or without a deaminase inhibitor, can be used with deoxyguanosine. It is believed that the selective action of MMdCyd is due to preferential inhibition of viral DNA polymerase and probably subsequent incorporation of MMdCyd in viral DNA. When used in combination with dGuo, H$_4$Urd or H$_4$dUrd, MMdCyd results in perturbation of dNTP pools. This in turn leads to deprivation and decreased used of dTTP and dCTP required for viral DNA synthesis.

As indicated above, the preferred compound of the invention is 5-methoxymethyl-2'-deoxycytidine (MMdCyd) and in what follows reference is made to this particular compound. It is believed, however, that the 5-alkoxymethyl analogues having up to 4 carbon atoms in the alkoxy group can also be used in place of MMdCyd. When the alkoxy group is propoxy or butoxy it can be straight or branched. It should be borne in mind when reading the following discussion other 5-alkoxymethyl compounds of the invention can be used.

It is believed that the proposed therapeutic regimen would have following advantages:

(i) Administration of 5-methoxymethyl-2'-deoxycytidine (MMdCyd) in combination with tetrahydrodeoxyuridine (H$_4$dUrd) would result in increased efficacy against HSV infections. Our hypothesis is that MMdCyd, co-administered with H$_4$dUrd, will be incorporated as such into the viral DNA. This approach is highly selective because it is directed specifically towards viral DNA.

(ii) Administration of MMdCyd in combination with deoxyguanosine (dGuo) should result in increased efficacy against HSV infections due to decreased viral DNA synthesis and failure of the virus to utilize DNA precursors.

(iii) Administration of MMdCyd in combination with deoxyguanosine (dGuo) and tetrahydrodeoxyuridine (H$_4$dUrd) would result in enhanced efficacy against HSV infections because of perturbation of dNTP pools, decreased viral DNA synthesis and direct incorporation of MMdCyd into viral DNA.

(iv) Administration of MMdCyd in combination with H$_4$dUrd and dGuo would result in reduced yield of infectious virus particles or in production of fraudulent virus particles with reduced capacity to cause new foci of infections.

(v) As an analogue of 5-methyl-2'-deoxycytidine, MMdCyd may interfere with the synthesis of nonmethylated DNA. Synthesis of nonmethylated DNA appears to play an important part in virus maturation and producing infection. Thus MMdCyd should have desirable effects in preventing latency or emergence of latency in recurrent infections. Specific indications and treatments are suggested below:

(1) MMdCyd for the treatment of Herpes simplex labialis and Herpes simplex keratitis. For this purpose the MMdCyd can be applied topically in a pharmaceutical composition with a suitable diluent or carrier, the MMdCyd preferably constituting from about 2 to about 20% by weight of the composition. (2) MMdCyd in combination with deaminase inhibitors, preferably tetrahydrodeoxyuridine or tetrahydrouridine, or MMdCyd plus deoxyguanosine for the treatment of Herpes simplex labialis and Herpes simplex keratitis. When using H$_4$dUrd or H$_4$Urd it is preferred to use about 10 mg to 200 mg per dose. When using dGuo it is preferred to use about 25 mg to 100 mg per dose. They can of course be administered with a pharmaceutically acceptable carrier. (3) MMdCyd in combination with tetrahydrodeoxyuridine for the treatment of primary Herpes simplex labialis (Herpes gingivostomatitis). Preferably the MMdCyd is administered by a parenteral route intraperitoneally or intramuscularly, in an amount of from 150 to 1,500 mg/kg/dose in a pharmaceutically acceptable carrier, and the amount of H$_4$dUrd is 25 to 100 mg/kg/dose. (4) MMdCyd in combination with tetrahydrodeoxyuridine for the treatment of Herpes simplex encephalitis. Preferably the MMdCyd is administered by a parenteral route intraperitoneally or intramuscularly, in an amount of from 150 to 1,500 mg/kg/dose in a pharmaceutically acceptable carrier, and the amount of H$_4$dUrd is 25 to 100 mg/kg/dose. (5) MMdCyd in combination with deoxyguanosine for the treatment of primary Herpes simplex labialis (Herpes gingivostomatitis). Preferably the MMdCyd is administered by a parenteral route, intraperitoneally or intramuscularly in an amount of from 150 to 1,500 mg/kg/dose in a pharmaceutically acceptable carrier and the dGuo is present in an amount of from 25 to 50 mg/kg/dose.

(6) MMdCyd in combination with deoxyguanosine for the treatment of Herpes simplex encephalitis. Preferably the MMdCyd is administered by a parenteral route, intraperitoneally or intramuscularly in an amount of from 150 to 1,500 mg/kg/dose in a pharmaceutically acceptable carrier and the dGuo is present in an amount of from 25 to 50 mg/kg/dose. (7) MMdCyd in combination with tetrahydrodeoxyuridine and deoxyguanosine for the treatment of primary Herpes simplex labialis (Herpes gingivostomatitis). Preferably the MMdCyd is administered by a parenteral route, intraperitoneally or intramuscularly in an amount of from 150 to 1,500 mg/kg/dose in a pharmaceutically acceptable carrier. (8) MMdCyd in combination with tetrahydrodeoxyuridine and deoxyguanosine for the treatment of Herpes simplex keratitis and Herpes simplex labialis. (9) MMdCyd in combination with tetrahydrodeoxyuridine and deoxyguanosine for the treatment of Herpes simplex encephalitis. Preferably the MMdCyd is administered by a parenteral route, intraperitoneally or intramuscularly in an amount of from 150 to 1,500 mg/kg/dose in a pharmaceutically acceptable carrier. (10) MMdCyd in combination with tetrahydrodeoxyuridine and deoxyguanosine for the treatment of primary Herpes simplex labialis (*Herpes gingivostomatitis*). Preferably the MMdCyd is administered by a parenteral route, intraperitoneally or intramuscularly in an amount of from 150 to 1,500 mg/kg/dose in a pharmaceutically acceptable carrier. (11) MMdCyd plus tetrahydrodeoxyuridine or MMdCyd plus deoxyguanosine for the prevention or treatment (in conjunction with other anticancer drugs) of malignancies such as nasopharyngeal carcinoma and uterine cervical carcinoma where Herpes simplex virus has been suggested as a probable causative agent. The anticancer drugs used for treatment of these cancers and in conjunction with which MMdCyd may be used, include methotrexate, 5-fluorouracil, cyclophosphamide, bleomycin and mitomycin.

It is believed that MMdCyd, co-administered with H4dUrd will be anabolized exclusively through virus-induced deoxycytidine kinase-deoxycytidylate kinase pathway in HSV-infected cells to their corresponding triphosphates. The MMdCTP will inhibit HSV-induced DNA polymerase by competing with deoxycytidine triphosphate (dCTP) (See Charts 1 and 2).

Chart 1.

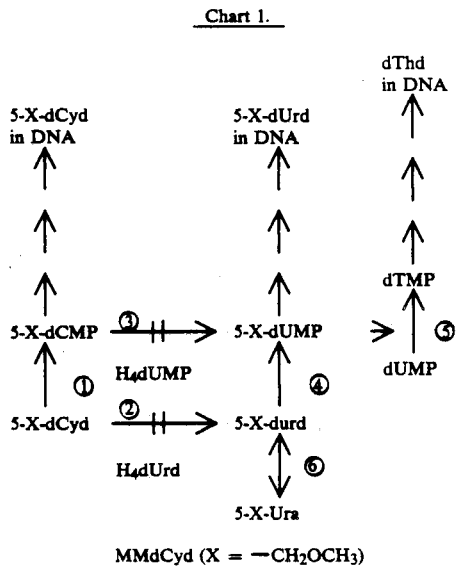

MMdCyd (X = —CH$_2$OCH$_3$)

Proposed pathways for transport and metabolism of MMdCyd in HSV-infected cells. Tetrahydro-deoxyuridine (H4dUrd) inhibits both cytidine deaminase and deoxycytidylate deaminase. Enzymes involved are: (1) dThd/dCyd kinase (virus-induced); (2) dCyd deaminase (inhibited by H4dUrd); (3) dCMP deaminase (virus induced) inhibited by H4dUMP; (4) dThd kinase (virus induced); (5) dTMP synthetase (inhibition of enzyme contributes to cytotoxicity); (6) dThd phosphorylase (breaks glycosidic bond).

MMdCYd would be incorporated as such into the viral DNA. As an analogue of 5-methyl-2'-deoxycytidine, MMdCyd is likely to interfere with the processes of synthesis of nonmethylated DNA. These processes appear to be an important part of virus maturation in productive infection as suggested by investigations of Sharma and Biswal (1977). The residual DNA synthesized in the presence of MMdCyd would contain substantial amounts of this nucleoside substituted instead of dCyd. DNA containing MMdCyd would behave in a similar manner as hyper-methylated DNA which is inactive. Thus MMdCyd should have desirable effects in preventing latency or emergence of latency in recurrent infections. In this respect the mode of action of MMdCyd is different from that of deoxyuridine analogues with antiherpes activity.

Co-administration of H4dUrd will prevent synthesis of dUMP from the deoxycytidine pool (See Chart 2, above). This would lead to diminished dTTP levels. Thus H4dUrd would potentiate antiviral activity of MMdCyd due to decreased production of an essential metabolite required for DNA polymerization.

The combination of H4dUrd with MMdCyd should be metabolically stable since dCyd and its analogues are not substrates of pyrimidine nucleoside phosphorylases. In contrast, deoxyuridine analogues are rapidly catabolized to pyrimidine bases by thymidine phosphorylase (Veres et al., 1986). This limits their therapeutic usefulness.

The cytotoxicity of deoxyuridine analogues is due to inhibition of thymidylate synthase by their corresponding monophosphates (DeClercq et al., 1982). MMdCyd should have low cytotoxic because combination with H4dUrd would utilize a different set of enzymes in anabolism (See Chart 1, above).

Penetration of MMdCyd in the CNS should be greater than its corresponding deoxyuridine derivative, 5-methoxymethyl-2'-deoxyuridine, because of its Chart 2.

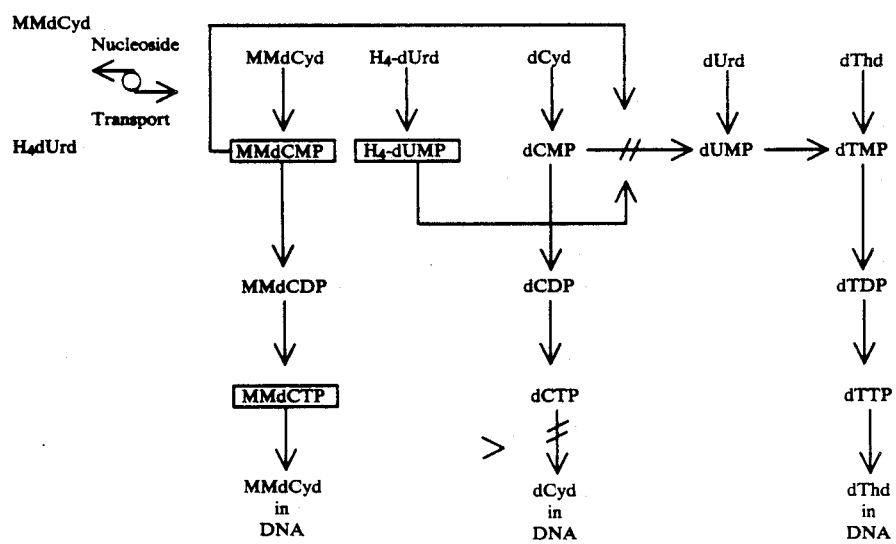

Pathways for incorporation of natural precursors, deoxythymidine (dThd) and deoxycytidine (dCyd) into DNA and suggested mechanisms for inhibition of this incorporation by 5-methoxymethyl-2'-deoxycytidine (MMdCyd) in combination with H4dUrd.

greater lipid solubility. This would be of considerable benefit particularly in the treatment of Herpes encephalitis, for which the response to therapy with approved drugs acyclovir and adenine arabinoside is suboptimal even if the treatment is instituted early (Whitley et al., 1986).

MMdCyd, co-administered with deoxyguanosine will lead to inhibition of viral DNA synthesis. This would arise primarily from the direct effects of dGuo (in a triphosphate form) on DNA polymerase in decreasing the utilization of dCTP and dTTP.

The combination of MMdCyd with deoxyguanosine and H4dUrd has the potential effect of diminishing dTTP pools, causing failure to utilize dCTP pools. This results in inhibition of viral DNA polymerase and subsequent incorporation of MMdCyd in viral DNA.

The invention is further illustrated with reference to the following examples and the accompanying figures. Of the figures:

FIG. 7 shows the structure of 4-triazolyl-5-methoxymethyl-3', 5'-diacetyl-2'-deoxy -1-β-D-ribofuranosylpyrimidine-2-one;

FIG. 8A and 8B are stereoscopic views of molecules A and B of MMdCyd;

Figure 10:
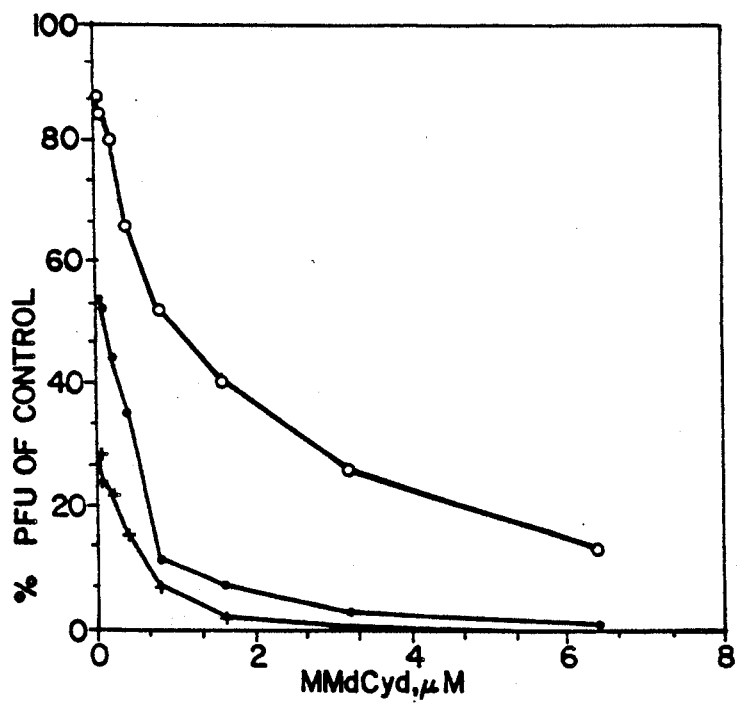
Figure 11:
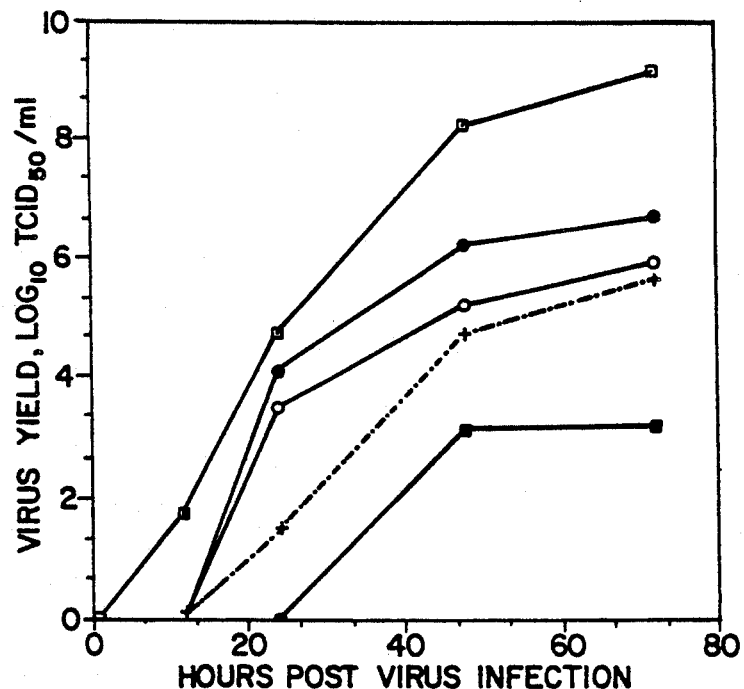
Figure 12:
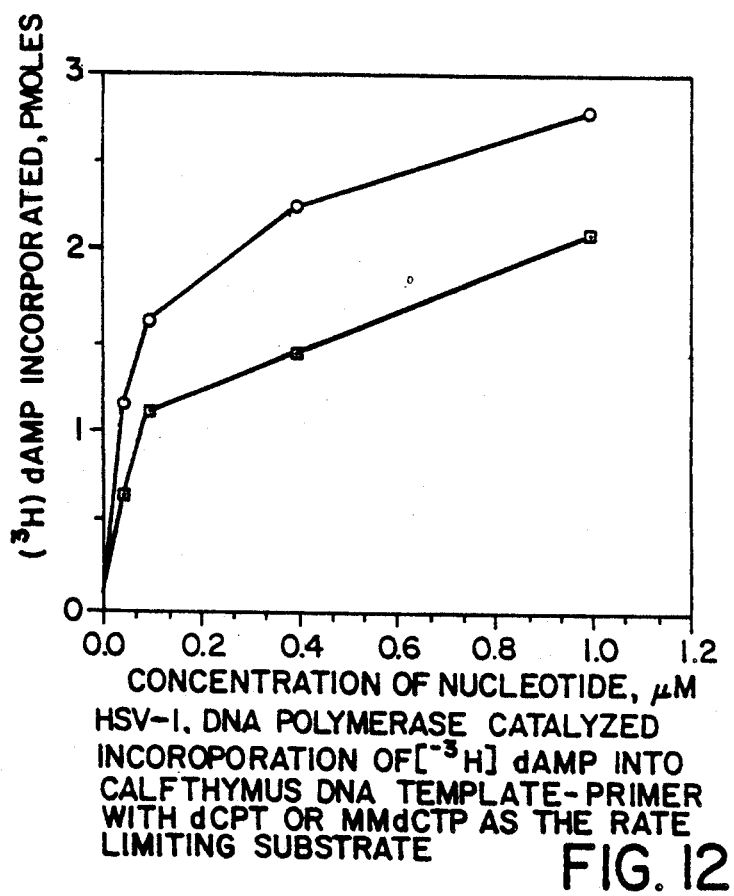
Figure 13:
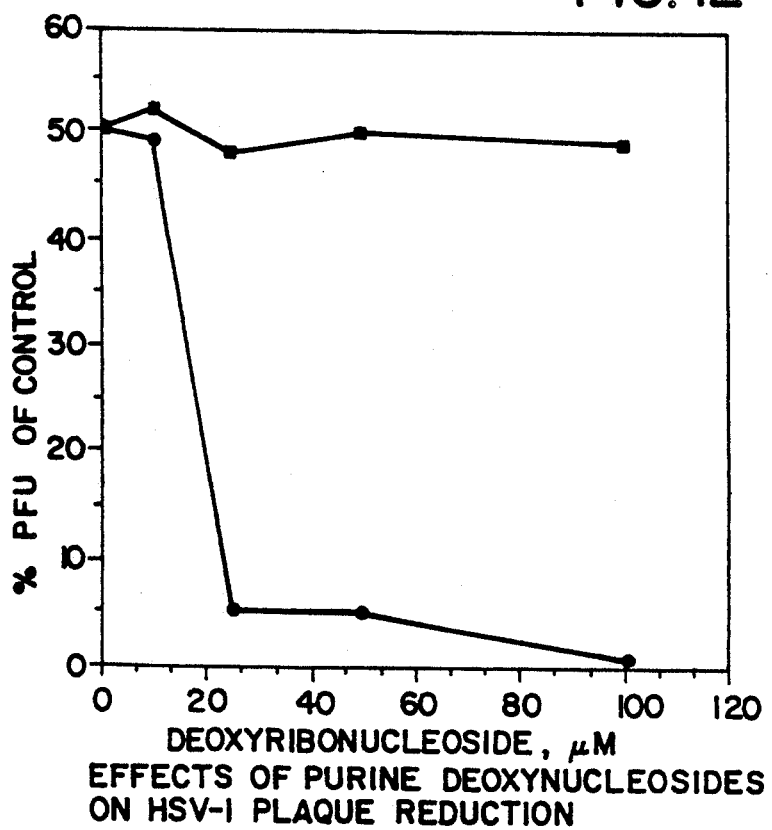

FIG. 10 graphically demonstrates potentiation of MMdCyd by dGuo and H4dUrd;

FIG. 11 shows the effect on production of infectious virus particles at different times of the infectious process by various treatments;

FIG. 12 demonstrates DNA polymerase catalyzed incorporation of [$^3$H] dAMP into calf thymus DNA template primer with dCTP or MMdCTP as the rate limiting substance;

FIG. 13 shows the effects of purine deoxynucleosides on HSV-1 plaque reduction.

Figure 14:
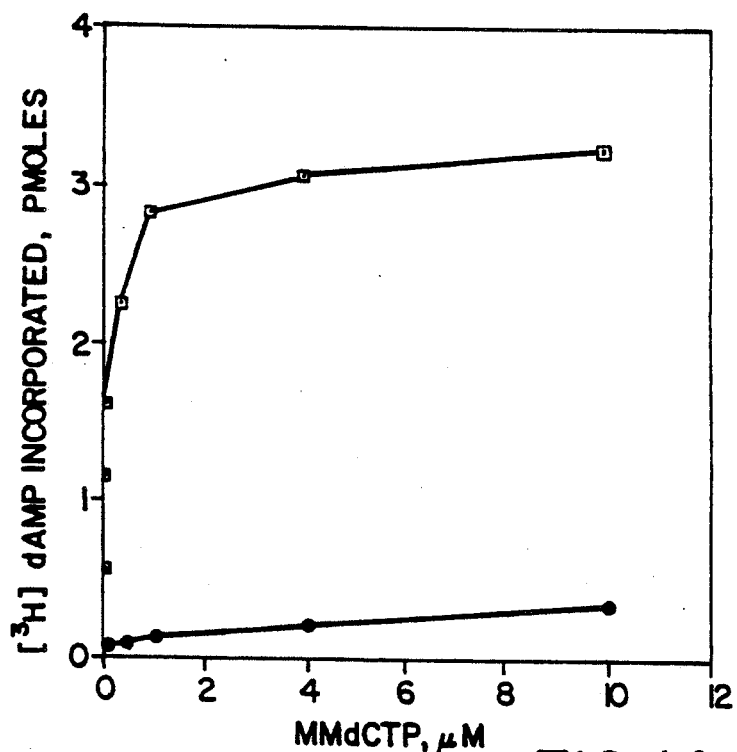

FIG. 14 graphically shows a comparison of in vitro DNA synthesis by viral and cellular DNA polymerases with MMdCTP as an alternative substrate (open squares, HSV-1 DNA polymerase: solid diamonds human DNA polymerase alpha).

Figure 15A:
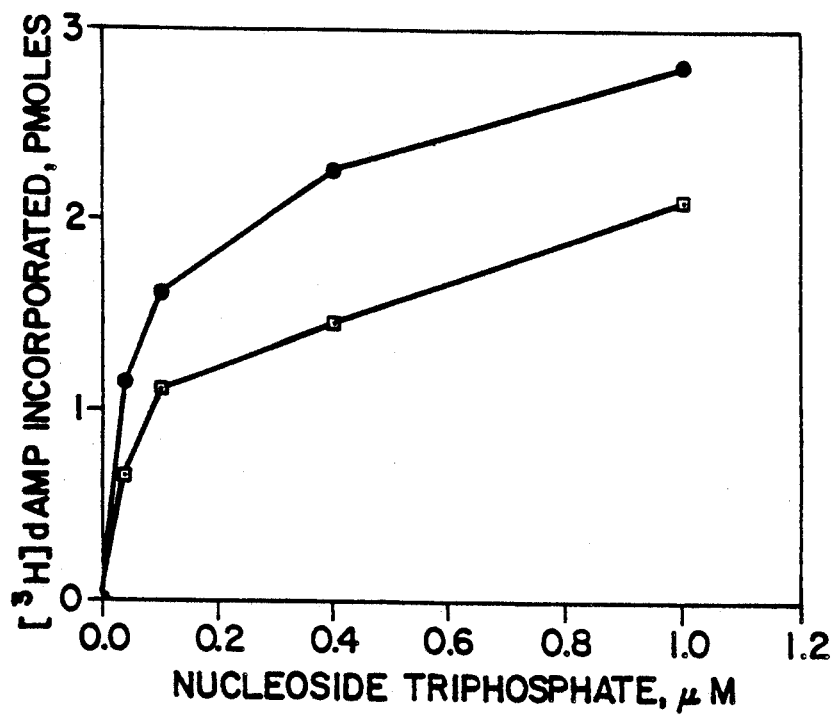

FIG. 15 demonstrates the effect of increasing the concentration of nucleoside triphosphate or its analogue on the incorporation in calf thymus DNA template-primer of [$^3$H] dAMP by HSV-1 DNA polymerase. In FIG. 15A solid diamonds represent utilization of MMdCTP and open squares represent utilization of dCTP. In FIG. 15A open triangles represent utilization of dTTP and crosses represent utilization of MMdUTP.

Figure 16:
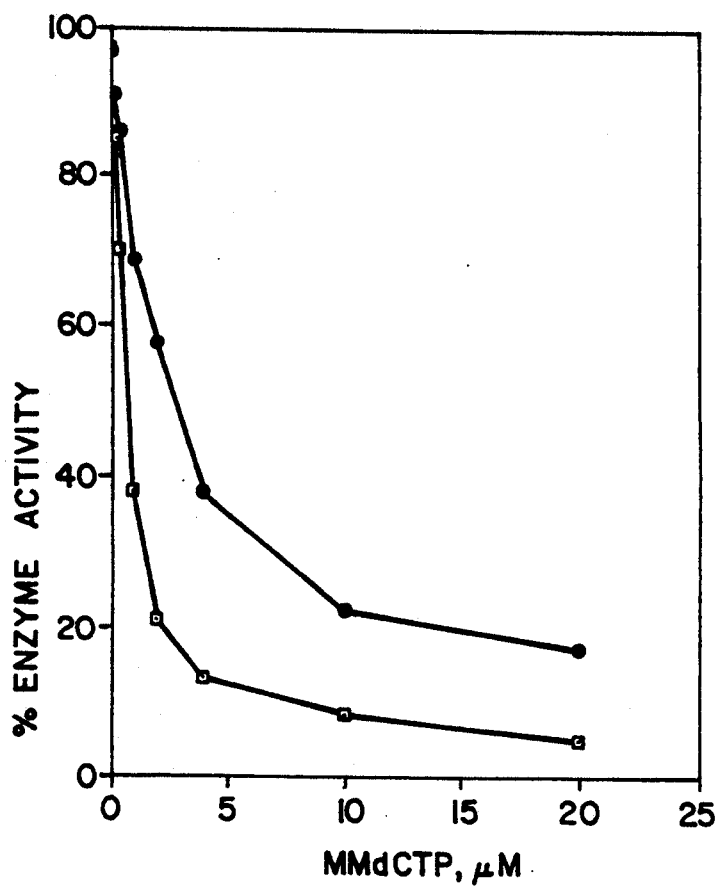

FIG. 16 shows inhibition of HSV-1and human DNA polymerase alpha by MMdCTP. Open squares show the HSV-1 DNA polymerase plot and solid diamonds show the human DNA polymerase alpha plot.

EXAMPLE 1

Synthesis of 5-Methoxymethyl-2'-deoxycytidine (MMdCyd) Triazole method

The synthesis of 5-methoxymethyl-2'-deoxycytidine (MMdCyd) from 5-methoxymethyl-2'-deoxyuridine (MMdUrd) was accomplished in four steps. Treatment of MMdUrd with acetic anhydride in pyridine gave 5-methoxymethyl-3',5'-diacetyl-2'-deoxyuridine (DiAcMMdUrd) in 75–86% yield. DiAcMMdUrd was added to a solution of 1,2,4-triazole, $POCl_3$ and triethylamine in acetonitrile to give 4-triazolyl-5-methoxymethyl-3',5'-diacetyl-2'-deoxy-1-β-D-ribofuranosylpyrimidine-2-one. The structure of this triazole derivative is shown in FIG. 7. The triazolyl derivative was dissolved in dioxane saturated with ammonia. After purification by silica gel chromatography ($CHCl_3$—$CH_3OH$ 90:10 eluant), 5-methoxymethyl-3',5'-diacetyl-2'-deoxycytidine (DiAcMMdCyd) was isolated (yield 80–90%). Deacetylation in methanolic-ammonia gave 5-methoxymethyl-2'-deoxycytidine (MMdCyd) in 75–80% yield; m.p. 171°–172° C. $R_f$ 0.3 (TLC, silica gel $CHCl_3$:MeOH 80:20), UV (0.1M HCl) $\lambda_{max}$ 284 nm (ε12,500), $\lambda_{min}$ 244 nm (ε1,300), 0.1M NaOH $\lambda_{max}$ 274 nm (ε8,300) and $\lambda_{min}$ 252 nm (ε5,500); $^1$HMR (DMSO—$d_6$) δ7.85, s, 1, 6—H; 7.35, 6.62, br peaks, 4—$NH_2$; 6.13, m, 1, 1'—H; 5.17, d, 1, 3'—OH; 4.98, t, 1, 5'—OH; 4.20, m, 1, 3'—H; 4.10, 4.07 pair d, 2, 5—$CH_2O$; 3.75, m, 1, 4'—H; 3.56, m, 2, 5'—H, 5"—H; 3.20, s, 3, $OCH_3$; 2.12, m, 2"—H; 1.94, m, 1, 2'—H. Anal. Calcd. for $C_{11}H_{17}N_3O_5$: C 48.70, H 6.32, N 15.49; Found; C 48.84, H 6.11, N 15.44.

EXAMPLE 2

DiAcMMdUrd dissolved in $CH_2Cl_2$ was added to a solution of $SOCl_2$ in dimethylformamide and the mixture was refluxed for 24 h. The resulting solution was treated with methanolic ammonia to yield MMdCyd in 25–30% yield.

Synthesis of N$^4$-Alkyl Derivatives

N$^4$-Alkyl derivatives of 5-methoxmethyl-2'-deoxycytidine are prepared by treating 4-triazolyl-5-methoxymethyl-3',5'-diacetyl-2'-deoxy-1-β-D-ribofuranosyl pyrimidine-2-one with the appropriate alkyl amine, for example, 5-methoxymethyl-N$^4$-methyl-2'-deoxycytidine was prepared in 70% yield using this method.

Synthesis of 5-Alkoxymethyl Derivatives

Analogous 5-alkoxymethyl derivatives such as 5-ethoxymethyl, 5-propoxymethyl, 5-butoxymethyl-2'-deoxycytidines are prepared by the same method starting from the appropriate 5-alkoxymethyl-2'-deoxyuridine precursor.

Synthesis of monophosphate Derivatives (General Procedure)

$POCl_3$ is slowly added to a solution of the nucleoside in trimethylphosphate at 4° C. and the reaction mixture is stirred at 4° C. for approx. 20 h. The monophosphorodichloridate solution obtained is slowly added to water, neutralized with triethylamine and extracted 3× with ethyl ether. The aqueous phase is chromotographed on a DEAE Sephadex A-25 (carbonate form) column and the effluent is monitored at 254 and 280 mn. After loading, the column is washed with water until the UV absorption returns to baseline and then eluted with 0.05M triethylammonium bicarbonate (pH 7.5). The eluant of appropriate fractions is pooled and evaporated. The example yield was 50% for 5-methoxymethyl-2'-deoxycyctidine-5'-monophosphate, UV (0.1M HCl) $\lambda_{max}$ 284 nm ($\epsilon$12,500) and 45% for 5-methoxymethyl-$N^4$-methyl-2'-deoxycyctidine-5'-monophosohate UV (0.1M HCl) $\lambda_{max}$ 283 nm ($\epsilon$13,900).

Syntheses of mono, di, triphosphasphate Derivatives
(General Procedure)

The 5' monophosphorodichloridate intermediate is prepared as described above. $POCl_3$ is slowly added to a solution of the nucleoside in trimethylphosphate at 4° C. The reaction mixture is stirred for approx. 20 h. and then slowly added to a solution of bis-(tributylammonium orthophosphate) in dimethyl formamide at 4° C. After stirring at room temperature for 3 h., water is added, neutralized with triethylamine and extracted 3× with ethyl ether. The mixture containing mono, di, tri and higher phosphates is loaded on a DEAE Sephadex A-25 (carbonate form) column, the column is washed with water until the UV absorption (monitored at 254 and 280 nm) returns to baseline. Elution with 0.05M triethylammonium bicarbonate elutes the monophosphate. Di, tri and higher phosphates are eluted with a linear gradient (0.05–0.5M) of triethylammonium bicarbonate (pH 7.5). Appropriate fractions are combined and lyophilized. For example, 5-methoxymethyl-2'-deoxycytidine and $N^4$-methyl-2'-deoxy-5-methoxymethyl-cytidine give corresponding phosphorylated compounds with an over all yield in the range of 30–35%. The relative amounts are monophosphate (14–18%); diphosphate (8–10%) and triphosphate (7–10%). Phosphorylated derivatives are approximately 90% pure as judged by HPLC.

EXAMPLE 3

The antiviral activity of MMdyCyd against HSV-1 and HSV-2 was demonstrated by infecting various cells with various strains of HSV-1 and HSV-2. Infected cells were treated with different concentrations of MMdCyd and the concentration required to reduce viral plaque formation by 50%, i.e. $ED_{50}$, was determined. Results are given in Table 1, below.

TABLE 1

Antiviral Activity of MMdCyd against Herpes simplex virus

| Virus Strain | Cell Line | PFU | $ED_{50}$ $(\mu M)^a$ |
|---|---|---|---|
| HSV-1 | | | |
| KOS | Vero | 20 | 14 |
| | | 50 | 26 |
| | Vero | 20 | 19 |
| | | 50 | 26 |
| NAH | Vero | 50 | 66 |
| | RK-13 | 10 | 3 |
| | | 50 | 5 |
| 76 | HEP-2 | 50 | 22 |
| TK | Vero | 10 | >833[b] |
| | | 50 | >833[b] |
| HSV-2 | | | |
| X-265 | Vero | 50 | 130 |
| 333 | Vero | 50 | 175 |

TABLE 1-continued

Antiviral Activity of MMdCyd against Herpes simplex virus

| Virus Strain | Cell Line | PFU | $ED_{50}$ $(\mu M)^a$ |
|---|---|---|---|
| MS | Vero | 50 | 228 |

[a]$ED_{50}$: Concentration required to reduce viral plaque formation by 50%.
[b]: Highest concentration tested.
PFU: plaque forming units.

EXAMPLE 4

Figure 1:
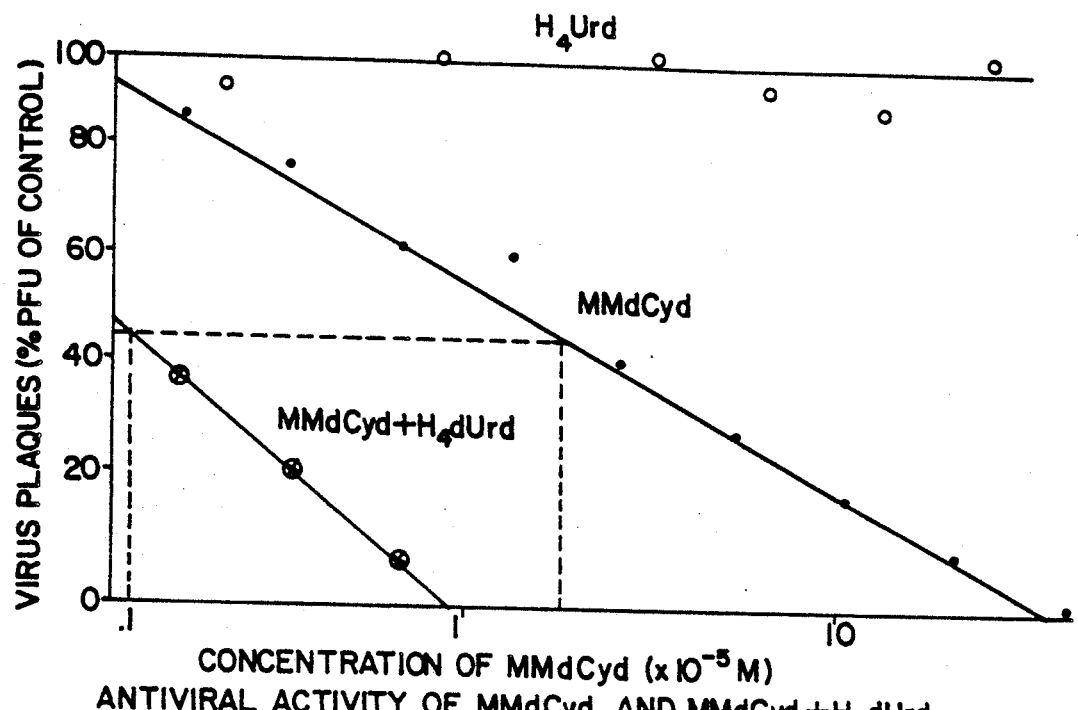
FIG. 1 is a graph showing antiviral acitivity of MMdCyd and MMdCyd+H4dUrd against HSV-1, KOS strain in Vero cells.

The antiviral activity of MMdCyd in the presence of the deaminase inhibitors $H_4Urd$ and $H_4dUrd$ was demonstrated. Vero cells were infected with the KOS strain of HSV-1. The compound of compounds indicated in Table 2, below, and are shown graphically in FIGS. 1, ($H_4dUrd$) and 2 ($H_4Urd$).

TABLE 2

Antiviral Activity[a] of MMdCyd in the Presence of Deaminase Inhibitors

| Compound | $ED_{50}$ $(\mu M)^b$ |
|---|---|
| MMdCyd | 12–17 |
| MMdCyd + $H_4Urd^c$ | 7.8–8.5 |
| MMdCyd + $H_4dUrd^d$ | 1.1–1.2 |

[a]Antiviral assays were carried out using Vero cells. All compounds were added immediately after virus infection.
[b]Concentrations required to cause 50% reduction in plaque numbers. HSV-1 Strain KOS; virus input 20 PFU.
[c]$H_4Urd$ - Tetrahydrouridine - inhibits deoxycytidine (Cyd/dCyd) deaminase. Amount used was 125 μg/ml.
[d]$H_4Urd$ - Tetrahydrodeoxyuridine - inhibits deoxycytidine (Cyd/dCyd) deaminase. Amount used was 125 μg/ml.

EXAMPLE 5

The antiviral activity of MMdCyd in the presence of $H_4dUrd$ was determined against several strains of HSV-1 and HSV-2. The results are summarized in Table 3.

TABLE 3

Antiviral activity of MMdCyd in the presence of $H_4dUrd$ against Herpes simplex virus types 1 and 2

| | HSV-1[a] | | | HSV-2[a] | | |
|---|---|---|---|---|---|---|
| Compound | KOS $ED_{50}(\mu M)^b$ | 76 | NAH | x-265 $ED_{50}(\mu M)^b$ | 333 | MS |
| MMdCyd | 26 | 26 | 66 | 130 | 175 | 228 |
| MMdCyd + $H_4dUrd$ | 1.1 | 1.2 | 15 | 60 | 98 | 110 |

[a]Antiviral assays were carried out using Vero cells. Virus input 50 PFU.
[b]$ED_{50}$: Concentration required to reduce viral plaque formation by 50%.

EXAMPLE 6

Vero cells were infected with HSV-1, strain 76 and treated with MMdCyd at different times post virus infection. The antiviral activity was demonstrated and results are summarized in Table 4.

TABLE 4

Antiviral activity of MMdCyd added at different time post virus infection

| Post Infection (Hours) | $ED_{50}^b$ $(\mu M)$ |
|---|---|
| 1 | 26 |
| 4 | 28 |

TABLE 4-continued

Antiviral activity of MMdCyd added at different time post virus infection

| Post Infection (Hours) | ED$_{50}$[b] ($\mu$M) |
|---|---|
| 6 | 32 |

[a]Antiviral assays were carried out in Vero cells using HSV-1 strain 76; Virus input 50 PFU.
[b]ED$_{50}$: Concentration required to reduce viral plaque formation by 50%.

EXAMPLE 7

Vero cells were infected with HSV-1, KOS strain and then treated with MMdCyd in various quantities, and also with MMdCyd in various quantities together with a constant amount of H$_4$dUrd. The virus infectivity was observed and the results are given in Table 5 and are shown graphically in FIG. 3.

TABLE 5

Effect of MMdCyd and MMdCyd + H$_4$dUrd on HSV-1, KOS, Infectivity Prior to Washing of Drugs

| Amount of MMdCyd ($\mu$M) | Virus Infectivity[a] (% of virus control) | |
|---|---|---|
| | MMdCyd treated cells | MMdCyd + H$_4$dUrd[b] treated cells |
| 0 (control) | 100 | 100 |
| 1.6 | 90 | 42 |
| 3.2 | 80 | 25 |
| 6.4 | 66 | 9 |
| 12.8 | 64 | 4 |
| 25.6 | 45 | 0 |
| 51.2 | 32 | 0 |
| 104 | 20 | 0 |
| 208 | 9 | 0 |
| 416 | 0 | 0 |
| 832 | 0 | 0 |

[a]Virus infectivity was scored using following parameters: rounding of cells, plaque formation and loss of monolayer structure.
[b]Concentration of H$_4$dUrd used was 530 $\mu$M (125 $\mu$g/ml). H$_4$dUrd alone did not exhibit antiviral activity at less than 2120 $\mu$M (500 $\mu$g/ml).

This example clearly demonstrates that MMdCyd reduces viral infectivity but the effect of MMdCyd is much enhanced when H$_4$dUrd is also present.

EXAMPLE 8

Vero cells were infected with HSV-1, KOS strain and then samples of the infected cells were treated with MMdCyd in various quantities and with MMdCyd in various quantities together with 530 $\mu$M of H$_4$dUrd. Cells were washed twice with 0.4 ml of MEM to remove residual drug, overlaid with growth medium and incubated for 72 h. The virus was harvested by two cycles of freezing and thawing. The culture fluid from each treatment was pooled and assayed for virus yield.

TABLE 6

Effect of MMdCyd and MMdCyd + H$_4$dUrd on HSV-1, KOS Infectivity After Removal of Drugs

| Amount of MMdCyd ($\mu$M) | Virus Infectivity[a] (% of virus control) | |
|---|---|---|
| | MMdCyd treated sample | MMdCyd + H$_4$dUrd[b] treated sample |
| 0 (control) | 100 | 100 |
| 1.6 | 100 | 85 |
| 3.2 | 99 | 73 |
| 6.4 | 99 | 60 |
| 12.8 | 99 | 47 |
| 25.6 | 99 | 37 |
| 51.2 | 70 | 22 |
| 104 | 55 | 14 |
| 208 | 40 | 1 |
| 416 | 20 | 1 |
| 832 | 10 | 0 |

[b]H$_4$dUrd 530 $\mu$M (125 $\mu$g/ml) was added along with MMdCyd. H$_4$dUrd did not exhibit antiviral activity up to 2120 $\mu$M.

Again, the results demonstrate that the MMdCyd is effective against the virus and the effectiveness of MMCyd is enhanced if H$_4$dUrd is also present.

EXAMPLE 9

Vero cells were treated with MMdCyd, H$_4$dUrd and MMdCyd+H$_4$dUrd. The cells were then assayed for the presence of deoxynucleoside triphosphates. Untreated Vero cells were also assayed for the presence of deoxynucleoside triphosphates, to provide a control. Results are given in Table 7.

TABLE 7

Effects of MMdCyd, H$_4$dUrd and MMdCyd + H$_4$dUrd on Deoxynucleoside Triphosphate (dNTP) Pools in Uninfected Vero Cells.[a]

| dNTP | Control | MMdCyd | H$_4$Urd | MMdCyd + H$_4$Urd | LSD[c] |
|---|---|---|---|---|---|
| | (pmoles/10$^6$ cells $\pm$ S.E.[b]) | | | | |
| dCTP | 15.6 $\pm$ 1.17 | 14.2 $\pm$ 1.30 | 30.8 $\pm$ 1.20 | 31.6 $\pm$ 1.87 | 1.86 |
| dTTP | 40 $\pm$ 1.23 | 44 $\pm$ 1.67 | 27.5 $\pm$ 1.25 | 32 $\pm$ 1.11 | 1.8 |
| dATP | 16.2 $\pm$ 0.9 | 8.3 $\pm$ 0.32 | 17.6 $\pm$ 1.28 | 17 $\pm$ 0.9 | 1.5 |
| dGTP | 19.3 $\pm$ 0.96 | 52 $\pm$ 1.84 | 32 $\pm$ 1.3 | 41 $\pm$ 1.04 | 2.24 |

[a]Cells were mock infected for one hour. Different treatments were given for seven hours.
[b]Values are means of at least two assays of triplicate cell extracts.
[c]Least significant difference.

EXAMPLE 10

Example 9 was repeated, except that the Vero cells subjected to the treatment had all been infected with HSV-1 KOS strain prior to the treatment. Results are given in Table 8.

TABLE 8

Effects of MMdCyd, H$_4$dUrd and MMdCyd + H$_4$dUrd on Deoxynucleoside Triphosphate (dNTP) Pools in Vero Cells Infected with Herpes Simplex Virus Type 1.[a]

| dNTP | Control | MMdCyd | H$_4$dUrd | MMdCyd + H$_4$dUrd | LSD[c] |
|---|---|---|---|---|---|
| | (pmoles/10$^6$ cells + S.E.[b]) | | | | |
| dCTP | 26 $\pm$ 1.18 | 29.6 $\pm$ 1.85 | 326 $\pm$ 12.6 | 43.2 $\pm$ 1.9 | 6.83 |
| dTTP | 303 $\pm$ 12.0 | 1072 $\pm$ 11.2 | 0.5 $\pm$ 0.34 | 93.6 $\pm$ 1.15 | 13.52 |
| dATP | 10.2 $\pm$ 0.34 | 25.2 $\pm$ 0.49 | 94.7 $\pm$ 2.06 | 59 $\pm$ 1.01 | 1.6 |

TABLE 8-continued

Effects of MMdCyd, H4dUrd and MMdCyd + H4dUrd on Deoxynucleoside Triphosphate (dNTP) Pools in Vero Cells Infected with Herpes Simplex Virus Type 1.[a]

| dNTP | Control | MMdCyd | H4dUrd | MMdCyd + H4dUrd | LSD[c] |
|---|---|---|---|---|---|
| | | (pmoles/10[6] cells ± S.E.[b]) | | | |
| dGTP | 67.8 ± 1.76 | 72.6 ± 2.07 | 101.3 ± 2.28 | 48.7 ± 1.24 | 2.4 |

[a]Cells were infected with 10 PFU/cell of HSV-1 KOS strain for one hour. Treatments were given for seven hours.
[b]Values are means of at least two assays of triplicate cell extracts.
[c]Least significant difference.

EXAMPLE 11

This example demonstrates the effect of pre-incubating infected cells[a] with H4dUrd prior to adding MMdCyd on Deoxyribonucleoside Triphosphate (dNTP) Pools.

TABLE 9

| dNTP | None | H4dUrd[b] | H4dUrd + MMdCyd[c] | LSD[e] |
|---|---|---|---|---|
| | | (pmoles/10[6] cells ± S.E.[d]) | | |
| dCTP | 26 ± 1.18 | 312 ± 10.1 | 29.8 ± 2.0 | 6.83 |
| dTTP | 303 ± 12 | 2 ± 0.41 | 108.6 ± 2.5 | 13.52 |
| dATP | 10.2 ± 0.34 | 119.4 ± 3.1 | 46.5 ± 1.2 | 1.6 |
| dGTP | 67.8 ± 1.76 | 141 ± 2.6 | 41.4 ± 1.4 | 2.4 |

[a]Cells were infected with 10 PFU/cell of HSV-1, KOS strain after which unadsorbed virus was removed by washing.
[b]H4dUrd in MEM was added immediately after adsorption and cells incubated for 2 hours. After this media containing H4dUrd was removed, cells washed and overlaid with fresh MEM.
[c]H4dUrd in MEM was added immediately after adsorption and cells incubated for 2 hours. After this, H4dUrd was removed, cells washed and overlaid with MMdCyd in MEM.
[d]Values are means of at least two assays of triplicate cell extracts.
[e]Least significant difference.

EXAMPLE 12

Vero cells and HSV-infected Vero cells were treated with dGUO and dGUO and H4dUrd. The cells were then assayed for the presence of deoxynucleoside triphosphates. Untreated Vero cells were also assayed for the presence of deoxynucleoside triphophate to provide a control. Results are summarized in Table 10.

TABLE 10

Effect of 2'-Deoxyguanosine on dNTP pools of MOCK-infected and HSV-infected Vero cells[a]

| Treatment dGUO (μM) | Deoxyribonucleosides (dNTP) | | | |
|---|---|---|---|---|
| | dCTP | dTTP | dGTP | dATP |
| | (pmoles/10[6] cells). | | | |
| Uninfected cells | | | | |
| 0 | 15 | 34 | 20 | 18 |
| 25 | 13 | 17 | 42 | 18 |
| 50 | 9 | 10 | 88 | 19 |
| 100 | 11 | 13 | 76 | 19 |
| 250 | 8 | 13 | 102 | 29 |
| 500 | 7 | 6 | 146 | 19 |
| HSV-infected cells | | | | |
| 0 | 23 | 129 | 52 | 12 |
| 25 | 23 | 110 | 290 | 12 |
| 50 | 33 | 118 | 373 | 12 |
| 100 | 64 | 214 | 600 | 12 |
| 250 | 78 | 233 | 558 | 14 |
| 500 | 60 | 247 | 738 | 25 |
| dGuO 100 μM + H4durd 1 mM | 129 | 27 | 290 | 34 |

[a]Cells were infected with 10 PFU/cell of HSV-1 KOS strain for one hour. Treatments were given for seven hours.

EXAMPLE 13

The antiviral activity, [a] cyctotoxicity* and antiviral indices of MMdCyd in the presence of H4dUrd, dGuo and H4dUrd+dGuo were determined. Results are given in Table 11.
*Cytotoxicity of MMdCyd:
Minimum cytotoxic concentrations (MTC) for MMdCyd was greater than 1,000 μg/ml for RK-13, HEP-2 and Vero cells.
Inhibitory effects of MMdCyd on the proliferation of murine and human tumor cells was also investigated. MTC for MMdCyd was greater than 400 μg/ml (highest concentration tested) against Raji, MOLT/4F, MT4, CEM and H-9 (human) and L1210 (murine Leukemia) cells.

TABLE 11

| Compound | ED50[b] (μg/ml) | | MTC[c] (μg/ml) | A.I[d] |
|---|---|---|---|---|
| MMdCyd | 6–12 | (8) | >1,000 | >125 |
| MMdCyd + H4dUrd[e] | 0.3–0.6 | (0.5) | >1,000 | >2,000 |
| MMdCyd + dGuo[f] | 0.3–0.6 | (0.5) | >1,000 | >2,000 |
| MMdCyd + dGuo + H[4]dUrd | 0.015–0.03 | (0.02) | >1,000 | >50,000 |

[a]Antiviral assays were carried out using Vero cells. Compounds were added immediately after virus infection. Virus HSV-1, strains KOS and 76; virus input: 50-100 PFU.
[b]ED50 = concentration required to cause 50% reduction in plaque numbers. Average values in bracket ( ).
[c]MTC = Minimum toxic concentration - concentration required to produce definite evidence of microscopic toxicity on confluent monolayer cells.
[d]AI = Antiviral indices - determined by dividing the MTC with ED50.
[e]Tetrahydrodeoxyuridine (H4dUrd) = Inhibitor concentration 125 μg/ml.
[f]Deoxyguanosine (dGuo) = Inhibitor concentration 25-30 μg/ml.

EXAMPLE 14

The survival and viability of Vero cells grown in the presence of 2'-deoxyguanosine, H4dUrd and deoxyguanosine+H4dUrd was determined. Results are given in Table 12.

TABLE 12

| Concentration of 2'-deoxyguanosine (μM) | Concentration of H4dUrd (μM) | Survival (viability) % |
|---|---|---|
| 0 | 0 | 100 |
| 25 | – | 100 |
| 50 | – | 100 |
| 100 | – | 100 |
| 250 | – | 100 |
| 500 | – | 88 |
| 1,000 | – | 63 |
| 0 | 1,000 | 100 |
| 100 | 1,000 | 87 |

EXAMPLE 15

The relative in vitro DNA synthesis by HSV-1 DNA Polymerase using dCTP or MMdCTP as the rate limiting substrate was determined. The synthesis was followed by assaying an incorporation of tritium labelled dAMP. The results are given in Table 13.

TABLE 13

| Unlabelled dNTP (μM) | Concentration of dCTP (μM) | Concentration of MMdCTP (μM) | Relative incorporation of [³H]dAMP++ (%)* |
|---|---|---|---|
| dGTP, dTTP | 10.00 | | 100 |
| dGTP, dTTP | 0.00 | 0.00 | 11 |
| dGTP, dTTP | 0.02 | | 22 |
| dGTP, dTTP | 0.04 | | 37 |
| dGTP, dTTP | 0.10 | | 55 |
| dGTP, dTTP | 0.40 | | 69 |
| dGTP, dTTP | 1.00 | | 94 |
| dGTP, dTTP | 4.00 | | 98 |
| dGTP, dTTP | | 0.02 | 34 |
| dGTP, dTTP | | 0.04 | 56 |
| dGTP, dTTP | | 0.10 | 75 |
| dGTP, dTTP | | 0.40 | 100.6 |
| dGTP, dTTP | | 1.00 | 140 |
| dGTP, dTTP | | 4.00 | 132 |
| dGTP, dTTP | | 10.00 | 130 |
| dGTP, dTTP | 0.40 | 0.40 | 100 |
| dGTP, dTTP | 10.00 | 10.00 | 138 |

+ unlabelled dNTP concentration 10 μM
++ Radio labelled [³H]dAMP conc 0.2 μM
*One hundred percent activity represents 27355 cpm of [³H]dAMP incorporation in the presence of 10 μM dCTP.

EXAMPLE 16

A kinetic analysis of MMdCTP inhibition of HSV-1 DNA Polymerase was conducted and results are given in Table 14.

TABLE 14

| Km(M) dCTP | Ki(M) MMdCTP | Km/Ki |
|---|---|---|
| $1.5 \times 10^{-7}$ | $3.8 \times 10^{-7}$ | 0.4 |

EXAMPLE 17

A comparison of in vitro DNA synthesis by viral and cellular DNA polymerases with MMdCTP as an alternative substrate. The results are shown graphically in FIG. 14 and compare HSV-1 DNA polymerase and human DNA polymerase alpha activity.

The number of pmoles of [³H] dAMP incorporated into control samples ('O'MMdCTP) was subtracted from pmoles of test samples. Other nucleotides, dATP, dTTP and dGTP were in excess (10 μm). Each assay was performed in triplicate.

The results show that the MMdCTP is readily utilized by the HSV-1 DNA polymerase but little used by the human DNA polymerase alpha (as measured by [³H] dAMP incorporation).

EXAMPLE 18

Figure 15B:
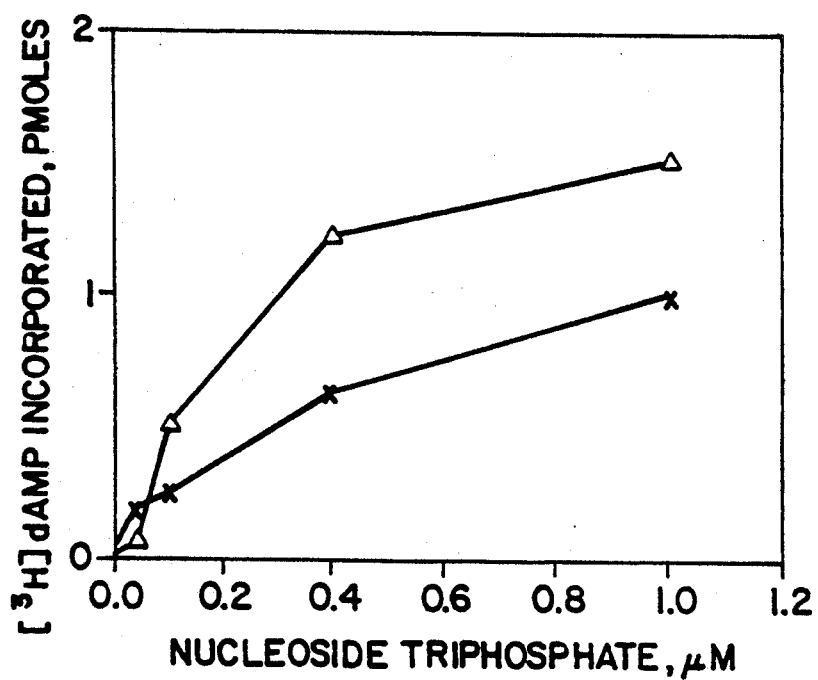

The effect of increasing the concentration of a nucleoside triphosphate or its analogue on the incorporation of [³H] dAMP by HSV-1 DNA polymerase into calf thymus DNA template-primer was studied. Each assay was carried out in triplicate and the results are shown in FIG. 15. In FIG. 15A the concentrations of dATP, dGTP and dTTP were in excess and in FIG. 15B the concentrations of dATP, dGTP and dCTP were in excess (10μM in each case).

The pmoles of [³H] dAMP incorporated in the control samples (three nucleotides only) were substrated from the pmoles of test samples.

EXAMPLE 19

The inhibition of HSV-1 and human DNA polymerase alpha by MMdCTP was studied and the results shown graphically in FIG. 16. Assay conditions were specific for each enzyme and each assay was performed in triplicate. As can be seen there is a clear difference in effect of MMdCTP on each enzyme.

DISCUSSION OF RESULTS

Antiviral Activity

Figure 2:
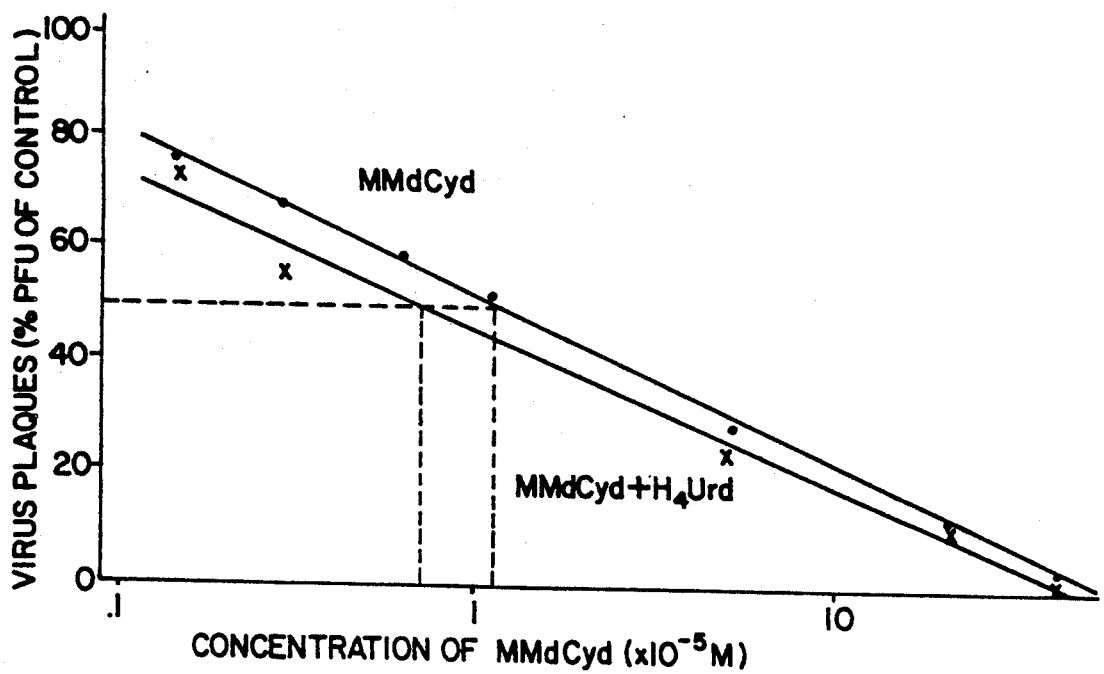
FIG. 2 is a graph showing antiviral activity of MMdCyd and MMdCyd+H4Urd against HSV-1, KOS strain in Vero cells.

1. Effect of MMdCyd and MMdCyd in combination with deaminase inhibitors against HSV replication MMdCyd is a selective inhibitor of HSV-1 with $ED_{50}$ (50% inhibitory concentration) values against HSV-1 strains ranging from 3 to 66 μM (See Table 1). The antiviral potency was higher in RK-13 cells ($ED_{50}$, 3 to 5 μM) and approximately 4 to 5 fold lower in Vero and HEP-2 cells ($ED_{50}$, 14–26 μM). MMdCyd was marginally active against HSV-2 ($ED_{50}$ 130 to 230 μM). The lack of activity against thymidine kinase negative strain (HSV—TK⁻) indicates that the activity of MMdCyd is dependent on the initial activation (phosphorylation) by the viral enzyme. Potency of MMdCyd was much greater in combination with H₄dUrd with $ED_{50}$ values in the range of 1 μM for HSV-1 strains KOS and 76 (See FIG. 1 and Tables 2 and 3). H₄dUrd inhibits both Cyd/dCyd deaminase and dCMP deaminase. In combination with H₄Urd (an inhibitor of Cyd/dCyd deaminase) the potency of MMdCyd was only slightly enhanced with $ED_{50}$ in the range of 7 to 8 μM (See FIG. 2 and Table 2). RK cells contain primarily dCMP deaminase (DeCLercq et al., 1981) and HEP-2 cells contain high levels of both Cyd/dCyd deaminase and dCMP deaminase (Fox et al., 1983). Since the antiviral activity in HEP-2 cells and Vero cells are similar, we believe Vero cells also have high levels of both Cyd/dCyd deaminase and dCMP deaminase. On the basis of these results, it appears that in HSV-infected cells MMdCyd is most likely metabolized by the following pathway: Nucleoside pyrimidine kinase→deoxycytidine deaminase→deoxycytidylate deaminase pathway.

The observation that H₄Urd potentiated the activity of MMdCyd by approximately 2-fold suggests that, in the presence of H₄Urd inhibitor, MMdCyd was phosphorylated, without deamination, to MMdCMP and that the nucleotide was probably subsequently deaminated to MMdUMP by deoxycytidylate deaminase. In contrast, in combination with H₄dUrd, MMdCyd was most probably metabolized by the dCyd kinase→dCMP kinase in virus infected cells. When the time of onset of treatment was delayed for 4 to 6 hours post virus infection, $ED_{50}$ values were essentially similar as one hour post virus infection (Table 4). These results are significant because they indicate that delay up to 6 hours post infection does not seem to affect the processing of MMdCyd for antiviral activity.

2. Effect of MMdCyd in combination with deoxyguanosine and MMdCyd plus deoxyguanosine and tetrahydrodeoxyuridine against HSV replication MMdCyd is a potent inhibitor of HSV-1 with $ED_{50}$ values against HSV-1 in the range of 0.015 to 0.03 μg/ml (average 0.02 μg/ml) when used in combination with deoxyguanosine and tetrahydrodeoxyuridine (See FIG. 10 and Table 10). In FIG. 10 the legend is as follows: MMdCyd+dGuo —O—O— ($ED_{50}$ 0.3 μg/ml). Vero cells were incubated with H₄dUrd for 2 h, washed with MEM to remove H₄dUrd and then MMdCyd and dGuo were added —●—● ($ED_{50}$ 0.03 μg/ml). All compounds were added simultaneously, MMdCyd+H₄dUrd+dGuo x—x—x (ED₅₀ 0.016 μg/ml). Antiviral assays were carried out using Vero cells. ED₅₀=concentration required to reduce plaques by 50%. Virus input=100 PFU.

3. Effect of MMdCyd and MMdCyd plus inhibitor on virus yield

Figure 3:
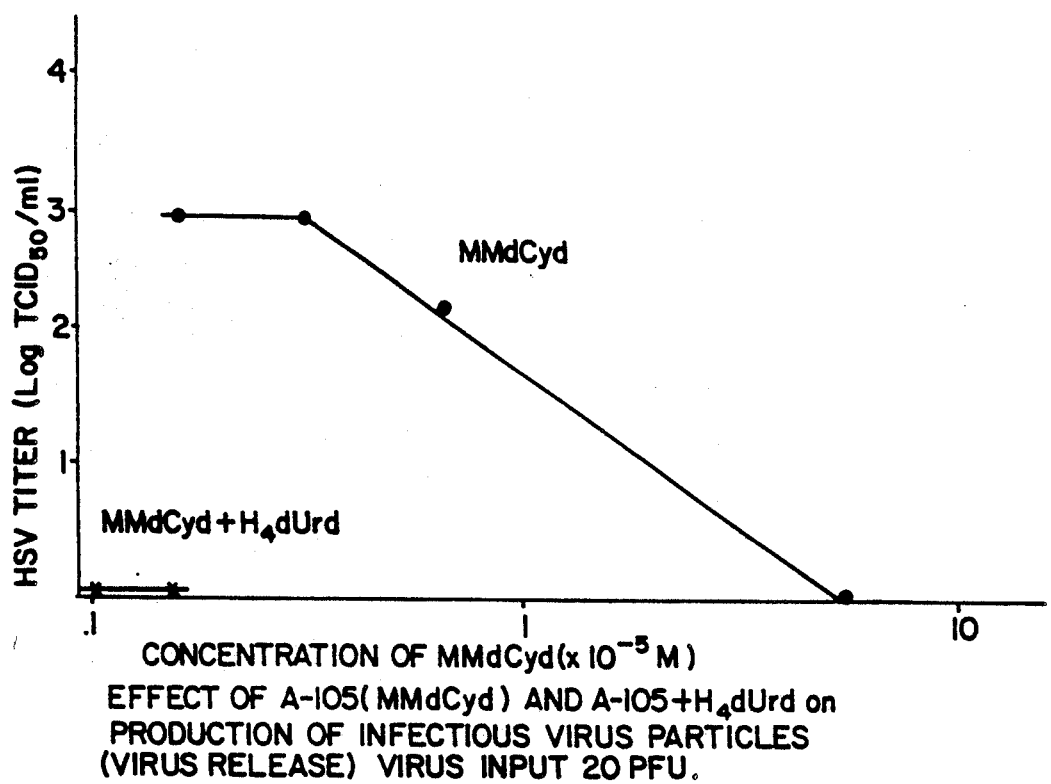
FIG. 3 is a graph showing the effect of MMdCyd and MMdCyd+H4dUrd on production of infectious virus particles.

The ability of MMdCyd to inhibit production of infectious virus particles was investigated by virus-yield studies (See FIG. 3 and Tables 5 and 6). The production of infectious virus particles significantly decreased on treatment with MMdCyd and was completely inhibited by MMdCyd (>12 μM) in combination with 530 M H₄dUrd (See Table 5). H₄dUrd has no antiviral activity up to 2,120 μM (highest concentration tested).

After washing of drugs and incubation of cells in fresh maintenance medium, no decrease in virus infectivity was observed in cells treated with less than 26 μM MMdCyd. However, in combination with H₄dUrd, decrease in virus infectivity was observed at a concentration of 1.6 μM MMdCyd (See Table 6).

Potentiation of antiherpes activity of MMdCyd is further supported by reduction in production of infectious virus particles on exposure to different treatment regimens. Results of virus yield at intervals are shown in FIG. 11 in which virus control —☐—☐—; MMdCyd ...●...●...; MMdCyd+H₄dUrd —◯—◯—; MMdCyd+dGuo—X—X—MMdCyd+H₄dUrd+dGuo —■—■—.

4. Cytotoxicity studies

Minimum toxic concentration (MTC) for MMdCyd against Raji, MOLT/4F, MTA, CEM and H-9 cells (human cell lines) and L1210 cells (murine leukemia) was greater than 400 μg/ml (highest concentration tested). MTC was greater than 1,000 μg/ml for RK-13, HEP-2 and Vero cells confluent monolayers (Table 11). Tetrahydrodeoxyuridine and deoxyguanosine were devoid of cytotoxicity up to 1 mM and 250 μM respectively against rapidly dividing Vero cells (Table 12).

Antiviral Index

The antiviral index for MMdCyd was greater than 50,000 when used in combination with tetrahydrodeoxyuridine and deoxyguanosine (Table 11, above).

Mechanism of Action of MMdCyd

(i) Effect on DNA precursor pools

After virus infection there is a rapid expansion of deoxyribonucleoside triphosphate (dNTP) pools. In HSV-1 infected Vero cells, the total dNTP content increases by four fold in relation to that found before infection. Treatment of HSV-infected Vero cells with H₄dUrd and MMdCyd in combination leads to very marked alterations in levels of dCTP and dTTP pool sizes in relation to treatments with MMdCyd alone and H₄dUrd alone. These results are consistent with the proposed hypothesis that when MMdCyd is used in combination with H₄dUrd, cells are deprived of the key metabolite dTTP which appears to play a regulatory role for viral DNA synthesis. It is interesting to note that none of the treatments have any significant effect on levels of dCTP or dTTP pool sizes in mock-infected cells. Results are summarized (See Tables 7 to 9).

(ii) DNA synthesis using HSV-1 Purified DNA Polymerase

MMdCyd triphosphate is preferred as a substrate to dCTP (natural metabolite) for HSV-1 induced DNA polymerase. Relative rates of DNA synthesized in the presence of dCTP and MMdCTP are shown in FIG. 12 (open squares relate to the use of dCTP and solid diamonds relate to the use of MMdCTP) and Table 13. This is very significant finding because to our knowledge, no antiherpes compound is known with this unique characteristic.

MMdCTP is a potent inhibitor of viral DNA polymerase with Ki of $3.8 \times 10^{-7}$ M (See Table 14).

Effect of nucleosides on the Antiviral Activity of MMdCyd

(i) Purine Nucleosides

Antiviral activity of MMdCyd was markedly potentiated in the presence of deoxyguanosine. Maximal increase in antiherpes activity was seen at 100 μM of deoxyguanosine (See FIG. 13, solid circles). Deoxyadenosine had no effect on antiherpes activity of MMdCyd (See FIG. 13, open squares). In the experiments illustrated by FIG. 13 the amount of MMdCTP used with each concentration of purine was 8.5 μg/ml. Antiviral assays were carried out using vero cells, HSV-1 virus strains KOS and 76. Virus input was 20 PFU.

(ii) Pyrimidine Nucleosides

Figure 4:
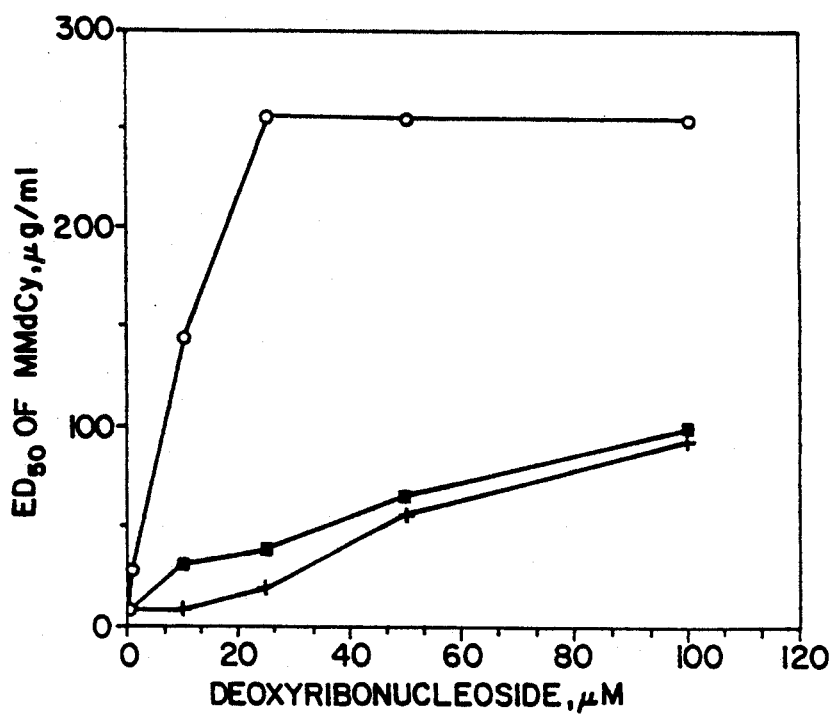
FIG. 4 is a graph of $ED_{50}$ values for MMdCyd against concentration of deoxyribonucleosides, demonstrating the reversal of the antiviral potency of MMdCyd by natural pyrimidine deoxynucleosides.
Figure 5:
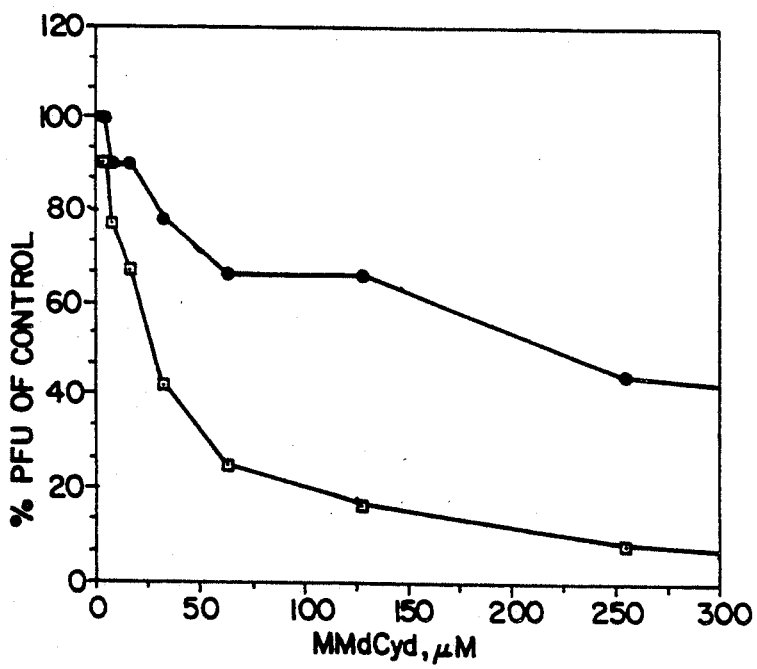
FIG. 5 is a graph of antiviral activity against concentration of MMdCyd, showing reversal of the antiviral activity of MMdCyd by 2'-deoxycytidine.
Figure 6:
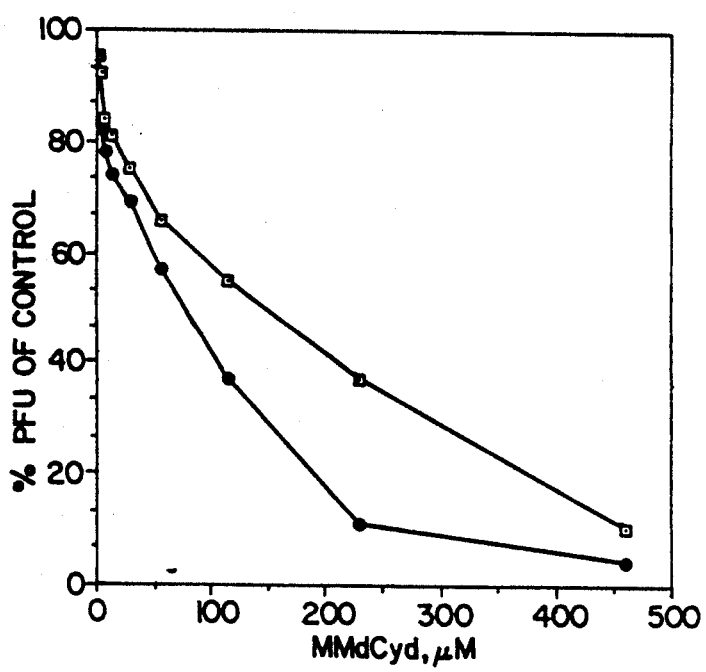
FIG. 6 is a graph of antiviral activity against concentration of MMdCyd, showing reversal of the antiviral of MMdCyd by 2'-deoxyuridine.

The antiviral activity of MMdCyd was reversed by pyrimidine nucleosides with decrease in potency in the following order:

deoxythymidine>deoxyuridine>deoxycytidine (See FIGS. 4 to 6). In FIG. 4, open circles denote deoxythymidine, solid squares denote deoxyuridine and plus signs indicate 2'-deoxycytidine. Since MMdCyd is a structural analog of deoxycytidine, the effect of dCyd was further investigated and results are shown in FIG. 5. In FIG. 5, open squares denote MMdCyd alone and solid circles denote equimolar concentrations of MMdCyd and dCyd. Equimolar concentrations of dCyd caused a parallel upward shift in the dose-response curve. These results suggest that reversal of activity, in part, may be due to interference at the transport level across the plasma membrane. This was further supported by studies utilizing deoxyuridine (See FIG. 6). In FIG. 6 open squares denote MMdCyd and 25 μM of dUrd, all components added simultaneously (ED₅₀=38 μg/ml), and solid diamonds denote MMdCyd added after preincubating the cells for 3 hours with 25 μm of dUrd, then washing dUrd (ED₅₀=21 μg/ml).

Derivatives of MMdCyd

5-Methoxymethyl-N⁴-methyl-2'-deoxycytidine (N-methyl MMdCyd)

A major drawback for the therapeutic use of cytidine compounds is their tendency to undergo deamination in the presence of deaminating enzymes. The problem of deamination can be overcome by using either deaminase inhibitors or by modification of the molecule to induce resistance to deaminases. Earlier studies have shown that alkylation of the 4-amino group of the pyrimidine moiety renders the molecule deaminase-resistant (Dollinger et al, 1967) Therefore 5-methoxymethyl-N⁴- methyl-2'-deoxycytidine (N-methyl-MMdCyd) was synthesized and its biological properties were investigated. Results are shown in Tables 15 to 18.

1. Antiviral Activity (i) N-methyl-MMdCyd was found to be devoid of antiviral activity up to 1796 μM. The lack of bioactivity of N-methyl MMdCyd could be due to the fact that this molecule is not phosphorylated by the HSV-induced dThd/dCyd kinase.

(ii) 5-Methoxymethyl-$N^4$-methyl-2'-deoxycytidine-5'-monophosphate (N-methyl-MMdCMP): N-methyl-MMdCMP was completely inert against HSV-1 and HSV-2. Results of antiviral activity are given in Table 15.

2. Mechanism of action of N-methyl-MMdCyd

Effect of N-methyl-MMdCyd on deoxyribonucleoside triphosphate (dNTP) pools and its utilization as a substrate for DNA synthesis using *E. coli*, Human and HSV-1 DNA polymerase was investigated. Results are summarized below.

(i) Effect of N-methyl-MMdCyd on deoxyribonuceoside triphosphate pools

Vero cells were treated with N-methyl-MMdCyd. The cells were then assayed for dNTP pools. Results are given in Table 16. $N^4$-methyl-MmdCyd did not cause perturbation of dNTP pools to any significant degree.

(ii) DNA synthesis using *E. coli*, HSV-1 and Human DNA polymerase N-methyl-MMdCTP did not serve as a substrate for *E. coli* DNA polymerase. N-methyl-MMdCTP also did not interfere with incorporation of dCTP into DNA. Results are summarized (Table 17). N-methyl-MMdCTP was not incorporated into DNA by HSV-1 DNA polymerase and Human α-DNA polymerase (Table 18). Under similar conditions, dCTP served as an excellent substrate for DNA synthesis.

These results indicate that presence of the methyl group alters conformation of the molecule in such a manner that the nucleoside does not serve as a substrate for the HSV-induced dThd/dCyd kinase and its triphosphate does not serve as a substrate or inhibitor for DNA polymerase.

5-methyoxymethyl-2'-deoxycytidine-5'-monophosphate (MMdCMP)

MMdCMP was a potent inhibitor of HSV-1 (Table 15). These results indicate that phosphorylated compound are able to penetrate HSV-infected cells. Potency of MMdCMP is 2 to 3 times greater than its corresponding nucleoside indicating that MMdCMP most likely does not get dephosphorylated at the membrane prior to entry into HSV-infected cells.

3',5'-Diacetyl MMdCyd (DiACMMdCyd): This compound was synthesized because it could serve as a pro-drug and DiACMMdCyd may also penetrate better into the CNS because of its increased lipophilicity. Potency of DiACMMdCyd against HSV-1 was approximately 20 times lower than the parent compound in cell culture system (Table 15).

Antiviral activity of 5-Methyl-2'-deoxycytidine

Antiviral activity of 5-methyl-2'-dioxycytidine was determined against HSV-1 and results are shown in Table 15. 5-methyl-2'-deoxycytidine was devoid of activity up to 128 μg/ml. These results indicate that the nature of substituent at 5-position of the pyrimidine ring determine bioactivity. For example, a substituent, such as 5-methoxymethyl confers selectivity towards Herpes simplex virus, whereas the presence of methyl group renders the molecule inert against Herpes simplex virus.

X-Ray crystallographic studies

MMdCyd is a potent and selective antiherpes agent. In contrast, its $N^4$-methyl derivative (N-methyl-MMdCyd) was completely devoid of antiherpes activity. Studies have shown that the steric conformation of the deoxyribofuranose moiety is important in determining substrate specificity towards the viral enzyme. (Gupta et al, 1987). Therefore the crystal structure of MMdCyd and N-methyl-MMdCyd were determined.

Structure and conformation of MMdCyd $C_{11}H_{17}N_3O_5$ MMdCyd crystallized in space group $p^2{}_1$ with a=7.9255(6)Å; b=15.1505(15)Å, c=10.1861(5)Å, β=103.801(5)° and Z=4 (2 molecules per asymmetric unit); R=0.044 ($R_\omega$=0.046) for 2560 observed reflections with net $I>3\sigma(I)$. The furanose ring adopts the C(3')-exo envelope conformation ($_3E$) in molecule A and the C(2')-endo envelope conformation ($^2E$) in molecule B. In the sugar ring of both crystallographically-independent molecules A and B, the side chain at C(5') has the g+ conformation. This appears to be a preferred geometry required for antiherpes activity. The glycosyl linkage is anti with χ=213.7° for the A molecule and 222.2° for the B molecule. With respect to this anti conformation, the methoxy group at C(5) in molecules A and B exhibits different conformations; it is on the same side of the pyrimidine plane as the deoxyribofuranose ring oxygen (O4') in molecule A and on the opposite side in molecule B. This provides direct evidence that there is some freedom of rotation about the C(5)—C(5,1) bond. The stereoscopic view of the molecules A and B of MMdCyd are shown in FIGS. 8A and 8B.

Figure 9:
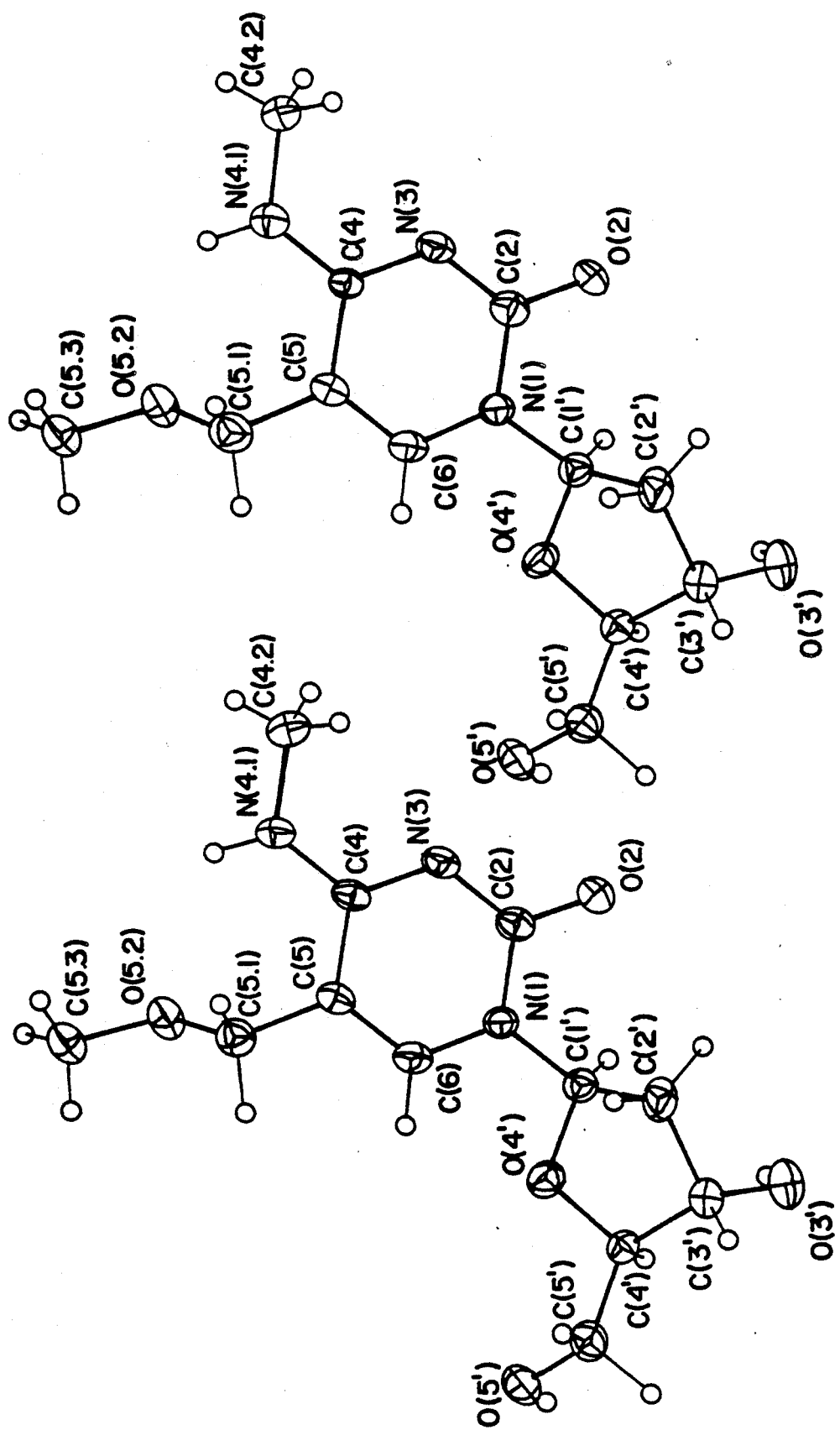
FIG. 9 is a stereoscopic view of a molecule of N-methyl-MMdCyd.

Structure and Conformation of N-methyl-MMdCyd $C_{12}H_{19}N_3O_5$, $M_r$=285.25, monoclinic, $P2_1$, a=7.0180(6), b=8.6946(11), c=10.7715(10)Å, β=91.055(7), V=657.15Å$^3$, Z=2, $D_x$=1.441 Mg m$^{-3}$, λ(Cu $K_x$)=1.5418Å, μ=1.32 cm$^{-1}$, F(000)=304, T=287 K, R=0.039 (wR=0.043) for 1424 observed reflections. The furanose ring adopts the C(1')-exo envelope conformation ($_1E$), with the glycosyl linkage being anti (χ=193.8°). The pseudorotational parameters are P=130.9° and $\tau_m$=39.4°. In the deoxyribose ring, the side chain on C(5') has the t conformation. The stereoscopic view of the molecule of N-methyl-MMdCyd is shown in FIG. 9. In the pyrimidine ring the $N^4$-methyl takes a Cis conformation to N(3) and the methoxymethyl side chain is on the same side of the cytidine plane as O(4').

X-ray crystallographic studies show that the side chain at C(5') in MMdCyd and N-Me-MMdCyd has different conformation. The altered conformation of the deoxyribofuranose moiety in N-Me-MMdCyd is possibly a reason for the loss of bioactivity of this molecule.

TABLE 15

Antiviral Activity[a] of MMdCyd and its Derivatives against Herpes Simplex Virus

| Compound | $ED_{50}$[b] ($\mu M$) |
|---|---|
| MMdCyd | 26 |
| MMdCMP | 10–14 |
| N-Me-MMdCyd | >1796[c] |
| N-Me-MMdCMP | >1796[c] |
| Di-AC-MMdCyd | 535 |
| MedCyd | >530[c] |

[a]Antiviral assays were carried out in Vero cells using HSV-1 strain KOS, virus input = 50 PFU
[b]$ED_{50}$ = concentration required to reduced viral plaque formation by 50%
[c]Highest concentration tested. No reduction in virus plaques was observed.

TABLE 16

Effect of N-MeMMdCyd on Deoxyribonucleoside Triphosphate Pools of Uninfected and HSV-1 Infected Vero Cells

| Treatment | Deoxyribonucleoside Triphosphate (dNTP) | | | |
|---|---|---|---|---|
| | dCTP | dTTP | dATP | dGTP |
| | ($pmoles/10^6$ cells $\pm$ S.E.)[a] | | | |
| Uninfected Vero Cells[b] | | | | |
| Control | 15.6 $\pm$ 1.17 | 40 $\pm$ 1.23 | 16.2 $\pm$ 0.9 | 19.3 $\pm$ 0.96 |
| N-MeMMdCyd | 17.3 $\pm$ 1.32 | 38.6 $\pm$ 1.22 | 32.2 $\pm$ 2.5 | 36.3 $\pm$ 1.67 |
| HSV-Infected Vero Cells[c] | | | | |
| Control | 26 $\pm$ 1.18 | 303 $\pm$ 12 | 10.2 $\pm$ 0.34 | 67.8 $\pm$ 1.76 |
| N-MeMMdCyd | 18 $\pm$ 1.08 | 419 $\pm$ 10.6 | 7.4 $\pm$ 0.4 | 58.9 $\pm$ 2.22 |

[a]Values are means of at least six determinations. dNTP pools were determined 8 hours post infection. Standard errors ($\pm$S.E.)
[b]Cells were mock-infected for one hour. Treatment was given for seven hours.
[c]Cells were infected with 10 PFU/cell of HSV-1 strain KOS for one hour. Treatment was given for seven hours.

TABLE 17

Comparison of in vitro DNA synthesis when N-MeMMdCTP and dCTP are utilized as rate limiting substrates and the effects of N-MeMMdCTP on dCTP Utilization

| Nucleotide ($\mu M$) | cpm[$^3$H]dAMP Incorporated[b] | | |
|---|---|---|---|
| | N-MeMMdCTP | dCTP | N-MeMMdCTP[c] + dCTP |
| 0.039 | −18 | 35 | 44 |
| 0.078 | −7 | 118 | 110 |
| 0.156 | 3 | 216 | 219 |
| 0.312 | −9 | 527 | 528 |
| 0.625 | 3 | 1171 | 998 |
| 1.25 | −20 | 1603 | 1592 |
| 2.50 | −17 | 1554 | 1620 |
| 5.0 | −16 | 2032 | 2100 |

[a]Enzymatic assays were carried out with 1 unit of Sigma E. coli DNA Polymerase 1. dTTP, dGTP and [$^3$H] dATP were non limiting (5 $\mu M$).
[b]Values obtained are net after subtracting "0" samples which did not contain the nucleotide tested.
[c]Amount of N-MeMMdCTP used with each concentration of dCTP was 0.625 $\mu M$.

TABLE 18

Relative in vetro DNA synthesis by Viral of Cellular DNA Polymerases with dCTP of N4-MeMMdCTP as the Rate-Limiting Substrate

| Unlabelled dNTP ($\mu M$)[+] | dCTP ($\mu M$) | N-MeMMdCTP ($\mu M$) | Relative Incorporation of [$^3$H]dAMP DNA Polymerase[++] | |
|---|---|---|---|---|
| | | | HSV-1 (%) | Human (%) |
| dGTP, dTTP | 10 | | 100* | 100** |
| dGTP, dTTP | 0 | 0 | 12 | 38 |
| dGTP, dTTP | | 0.1 | 10 | 32 |
| dGTP, dTTP | | 0.4 | 10 | 28 |
| dGTP, dTTP | | 1 | 11 | 29 |
| dGTP, dTTP | | 4 | 13 | 31 |
| dGTP, dTTP | | 10 | 14 | 35 |
| dGTP, dTTP | 10 | 10 | 103 | 106 |

[+]unlabeled dNTP concentration (10 $\mu M$).
[++]0.2 $\mu M$ of [$^3$H]dATP was used in each assay.
*100% activity represents 27355 cpm of [$^3$H]dAMP incorporated in the presence of 10 $\mu M$ dCTP.
**100% activity represents 4059 cpm of [$^3$H]dAMP incorporated in presence of 10 $\mu M$ dCTP.

REFERENCES

Babiuk, L. A., J. B. Meldrum, V. S. Gupta and B. T. Rouse. Antimicrob. Agents Chemother. 8:643 (1975).

Corey, L., H. G. Adams, Z. A. Brown and K. K. Holmes. Annals Intern. Med. 98:958 (1983).

Corey, L. and P. G. Spears. New Engl. J. Med. 314:686 (1986).

DeClercq, E. Trends in Pharmacol. Sci. 3:492 (1982).

DeClercq, E., J. Descamps, P. Desomer, P. J. Barr, A. S. Jones and R. T. Walker. Proc. Natl. Acad. Sci. (USA) 76:2947 (1979).

Dollinger, M. R., J. H. Burchnenal and J. J. Fox, Biochem. Pharmacol. 16, 689 (1967).

Elion, G. B., P. A. Furnam, T. A. Fyte, P. de Miranda, L. Beauchamp and H. T. Schaeffer. Proc. Nat. Acad. Sci. (USA) 74:5716 (1977).

Fox, L., M. J. Dobersen and S. Greer. Antimicrob. Agents Chemother. 23:465 (1983).

Gupta, V. S. Treatment of Viral Infections. U.S. Pat. No. 4,148,889, issued Apr. 10, 1979. Canadian Patent No. 1,074,699, issued Apr. 1, 1980.

Gupta, V. S. Drugs of the Future. 6:32 (1981).

Gupta, V. S., Tourigny, G., Stuart, A. L., DeClercq, E., Quail, J. W., Ekiel, I, ElKabbani, O. A. and Delbaere, L. T. J. Antiviral Res 7, 69–77 (1987).

Helgstrand, E., B. Eriksson, B. Johansson et al. Science 201:819 (1978).

Hirsch, M. S. and R. T. Schooley. New Engl. J. Med 309(16):1034 (1983).

Kim, C. H., Marquez, V. E., Mao, D. T., Haines, D. R., and McCormick, J. J. J. Med. Chem. 29, 1375 (1986).

Liu, P. S., Marquez, V. E., Discole, J. S., and Fuller, R. W. J. Med. Chem. 24, 662 (1981).

Lopez, C., K. A. Watanabe and J. J. Fox. Antimicrob. Agents Chemother. 17:803 (1980).

Marquez, V. E., Liu, P. S., Kelley, J. A., Driscole, J. S. and McCormick, J. J. J. Med. Chem. 23, 713 (1980).

Maugh, T. H. Science 192:128 (1976).

Sharma, S. and N. Biswal. Virology 82:265 (1974).

Veres, Z., A. Szaboles, I. Szinai, G. Denes and A. Jeney. Biochmical Pharmacol. 35:1057 (1986).

Youssoufian, H., S. M. Hammer, M. S. Hirsch and C. Mulder. Proc. Natl. Acad. Sci. (USA) 79:2207 (1982).

Whitely, R. J., C. A. Alford, M. S. Hirsch et al. New Engl. J. Med. 314:144 (1986).

What we claim as our invention is:

1. A compound selected from the group consisting of 5-alkoxymethyl-2'-deoxycytidines, wherein the alkoxy group contains up to 4 carbon atoms, the 5'-monophosphates thereof, and the pharmaceutically acceptable salts and prodrugs thereof, wherein the prodrugs are selected from the group consisting of $N^4$-acylated compounds in which the acyl group is derived from an alkanoic acid having 3 to 7 carbon atoms.

2. A compound according to claim 2, which is 5-methoxymethyl-2'-deoxycytidine.

3. A method of combating infections caused by Herpes simplex virus, in a patient in need thereof said method comprising of administering to a patient an effective amount of a 5'-alkoxymethyl-2'-deoxycytidine wherein the alkoxy group contains up to 4 carbon atoms, or a 5'-monophosphate thereof, or a pharmaceutically acceptable salt or $N^4$-acylated prodrug thereof, wherein the acyl group is derived from an alkanoic acid having 3 to 7 carbon atoms.

4. A method according to claim 3, wherein the compound administered to the patient is 5-methoxymethyl-2'-deoxycytidine.

5. A method according to claim 4, wherein the compound is administered with a deaminase inhibitor selected from the group consisting of tetrahydrouridine and tetrahydrodeoxyuridine.

6. A method according to claim 5, wherein said deaminase inhibitor is tetrahydrouridine.

7. A method according to claim 5, wherein said deaminase inhibitor is tetrahydrodeoxyuridine.

8. A method according to claim 3, wherein there is also administered to the patient an amount of deoxyguanosine effective to potentiate the 5-alkoxymethyl-2'-deoxycytidine.

9. A method according to claim 4, wherein there is also administered to the patient an amount of deoxyguanosine effective to potentiate the 5-methoxymethyl-2'-deoxycytidine.

10. A method according to claim 5, wherein there is also administered to the patient an amount of deoxyguanosine effective to potentiate the 5-methoxymethyl-2'-deoxycytidine.

11. A method according to claim 6, wherein there is also administered to the patient an amount of deoxyguanosine effective to potentiate the 5-methoxymethyl-2'-deoxycytidine.

12. A method according to claim 7, wherein there is also administered to the patient an amount of deoxyguanosine effective to potentiate the 5-methoxymethyl-2'-deoxycytidine.

13. A composition comprising a 5-alkoxymethyl-2'-deoxycytidine, wherein the alkoxy group contains up to 4 carbon atoms, or a 5'-monophosphate thereof, or a pharmaceutically acceptable salt or $N^4$-acylated prodrug thereof, wherein the acyl group is derived from an alkanoic acid having 3 to 7 carbon atoms, together with a suitable diluent or carrier.

14. A composition according to claim 13, wherein said deoxycytidine is 5-methoxymethyl-2'-deoxycytidine.

15. A composition according to claim 14, which further comprises a deaminase inhibitor selected from the group consisting of tetrahydrouridine and tetrahydrodeoxyuridine.

16. A composition according to claim 15, wherein the deaminase inhibitor is tetrahydrouridine.

17. A composition according to claim 15, wherein the deaminase inhibitor is tetrahydrodeoxyuridine.

18. A composition according to claim 13, which further comprises deoxyguanosine in an amount effective to potentiate the 5-alkoxymethyl-2'-deoxycytidine.

19. A composition according to claim 14, which further comprises deoxyguanosine in an amount effective to potentiate the 5-methoxymethyl-2'-deoxycytidine.

20. A composition according to claim 15, which further comprises deoxyguanosine in an amount effective to potentiate the 5-methoxymethyl-2'-deoxycytidine.

21. A composition according to claim 16, which further comprises deoxyguanosine in an amount effective to potentiate the 5-methoxymethyl-2'-deoxycytidine.

22. A composition according to claim 17, which further comprises deoxyguanosine in an amount effective to potentiate the 5-methoxymethyl-2'-deoxycytidine.

* * * * *